US009289468B2

(12) United States Patent
Yang et al.

(10) Patent No.: US 9,289,468 B2
(45) Date of Patent: Mar. 22, 2016

(54) FUSION PROTEIN COMPRISING CIRCULARLY PERMUTED FORM OF TRAIL/APO2L, CODING GENE AND USE THEREOF

(75) Inventors: Shifang Yang, Beijing (CN); Junsheng Cui, Beijing (CN); Bing Zhu, Beijing (CN); Peng Wei, Beijing (CN)

(73) Assignee: Beijing Sunbio Biotech Co. Ltd., Beijing (CN)

( * ) Notice: Subject to any disclaimer, the term of this patent is extended or adjusted under 35 U.S.C. 154(b) by 0 days.

(21) Appl. No.: 14/344,289

(22) PCT Filed: Sep. 16, 2011

(86) PCT No.: PCT/CN2011/001573
§ 371 (c)(1),
(2), (4) Date: Mar. 24, 2014

(87) PCT Pub. No.: WO2013/037090
PCT Pub. Date: Mar. 21, 2013

(65) Prior Publication Data
US 2014/0342994 A1 Nov. 20, 2014

(51) Int. Cl.
| | |
|---|---|
| A61K 38/16 | (2006.01) |
| A61K 38/12 | (2006.01) |
| A61K 38/00 | (2006.01) |
| A61P 35/00 | (2006.01) |
| A61P 35/02 | (2006.01) |
| C07K 1/00 | (2006.01) |
| C07K 14/00 | (2006.01) |
| C07K 17/00 | (2006.01) |
| C07K 16/00 | (2006.01) |
| C12N 1/20 | (2006.01) |
| C12N 15/00 | (2006.01) |
| A61K 39/00 | (2006.01) |
| A61K 39/385 | (2006.01) |
| A61K 38/17 | (2006.01) |
| C07K 14/715 | (2006.01) |
| C07K 14/47 | (2006.01) |
| C07K 14/525 | (2006.01) |
| C12N 15/63 | (2006.01) |
| C12N 15/62 | (2006.01) |
| C07K 14/705 | (2006.01) |
| A61K 45/06 | (2006.01) |
| C07K 14/52 | (2006.01) |

(52) U.S. Cl.
CPC ............ *A61K 38/1761* (2013.01); *A61K 45/06* (2013.01); *C07K 14/47* (2013.01); *C07K 14/4747* (2013.01); *C07K 14/52* (2013.01); *C07K 14/525* (2013.01); *C07K 14/70575* (2013.01); *C07K 14/7151* (2013.01); *C12N 15/62* (2013.01); *C12N 15/63* (2013.01); *A61K 38/00* (2013.01); *C07K 2319/21* (2013.01); *C07K 2319/33* (2013.01)

(58) Field of Classification Search
None
See application file for complete search history.

(56) References Cited

U.S. PATENT DOCUMENTS

| | | | |
|---|---|---|---|
| 6,030,945 A | 2/2000 | Ashkenazi | |
| 6,284,236 B1 | 9/2001 | Wiley et al. | |
| 6,740,739 B1 | 5/2004 | Ashkenazi et al. | |
| 6,746,668 B2 | 6/2004 | Ashkenazi | |
| 6,998,116 B1 | 2/2006 | Ashkenazi | |
| 7,666,989 B2* | 2/2010 | Zhu ............................. | 530/350 |
| 8,395,166 B2 | 3/2013 | Seo et al. | |
| 2004/0001835 A1* | 1/2004 | Woessner et al. .......... | 424/155.1 |
| 2008/0280821 A1 | 11/2008 | Zhu | |

FOREIGN PATENT DOCUMENTS

| | | |
|---|---|---|
| CN | 1448404 A | 10/2003 |
| CN | 1448405 A | 10/2003 |
| CN | 101717449 A | 6/2010 |
| JP | 2007-536891 A | 12/2007 |
| JP | 2010-220623 A | 10/2010 |
| JP | 2011-508445 A | 3/2011 |
| KR | 10-2006-0088569 A | 8/2006 |
| WO | 03/029420 A2 | 4/2003 |
| WO | 2005/042744 A1 | 5/2005 |
| WO | 2010/010051 A1 | 1/2010 |

OTHER PUBLICATIONS

Arnau et al., Prot. Express. Purif. 48:1-13 (2006).*
Barlogie et al., Blood 103:20-32 (2004).*
PCT International Search Report of the International Searching Authority dated Jul. 5, 2012 for International Application No. PCT/CN2011/001573, English Translation, 6 pages.
J. F. R. Kerr et al., Apoptosis: A Basic Biological Phenomenon with Wide-Ranging Implications in Tissue Kinetics, British Journal of Cancer, 1972, vol. 26, No. 4, pp. 239-257.
Andrew G. Renehan et al., The relevance of apoptosis for cellular homeostasis and tumorigenesis in the intestine, Canadian Journal of Gastroenterology, Mar. 2001, vol. 15, No. 3, pp. 166-176.
Deepak Nijhawan et al., Apoptosis in Neural Development and Disease, Annual Review of Neuroscience, 2000, vol. 23, pp. 73-87.
Joseph T. Opferman and Stanley J. Korsmeyer, Apoptosis in the development and maintenance of the immune system, Nature Immunology, May 2003, vol. 4, No. 5, pp. 410-415.
Barbara A. Osborne, Apoptosis and the maintenance of homeostasis in the immune system, Current Opinion in Immunology, 1996, vol. 8, pp. 245-254.
Frederik H. Igney and Peter H. Krammer, Immune escape of tumors: apoptosis resistance and tumor counterattack, Journal of Leukocyte Biology, Jun. 2002, vol. 71, pp. 907-920.
Richard M. Locksley et al., The TNF and TNF Receptor Superfamilies: Integrating Mammalian Biology, Cell, Feb. 23, 2001, vol. 104, pp. 487-501.

(Continued)

*Primary Examiner* — James H Alstrum Acevedo
*Assistant Examiner* — Thea D' Ambrosio
(74) *Attorney, Agent, or Firm* — Fitch, Even, Tabin & Flannery, LLP

(57) ABSTRACT

Provided is a fusion protein comprising circularly permuted form of TRAIL, and the fusion protein contains circularly permuted form of TRAIL and oligopeptides located at the N-terminus and/or C-terminus of the permuted form. The oligopeptides contain a repeating sequence consisting of 3-10 histidines. The components of the circularly permuted form of TRAIL from N-terminus to C-terminus are: (a) amino acids 135-281 of TRAIL, (b) a linker, and (c) amino acids 121-135 of TRAIL or amino acids 114-135 of TRAIL or amino acids 95-135 of TRAIL or any fragments of amino acids 95-135 of TRAIL containing amino acids 121-135 of TRAIL. Also provided is a method for treating cancer by using the fusion protein.

14 Claims, 12 Drawing Sheets

(56) References Cited

OTHER PUBLICATIONS

Yves Chicheportiche et al., TWEAK, a New Secreted Ligand in the Tumor Necrosis Factor Family That Weakly Induces Apoptosis, The Journal of Biological Chemistry, Dec. 19, 1997, vol. 272, No. 51, pp. 32401-32410.

Avi Ashkenazi and Vishva M. Dixit, Death Receptors: Signaling and Modulation, Science, Aug. 1998, vol. 281, pp. 1305-1308.

Marcus E. Peter and Peter H. Krammer, Mechanisms of CD95 (APO-1/Fas)-mediated apoptosis, Current Opinion in Immunology, 1998, vol. 10, pp. 545-551.

Ayoub Suliman et al., Intracellular mechanisms of TRAIL: apoptosis through mitochondrial-dependent and -independent pathways, Oncogene, 2001, vol. 20, pp. 2122-2133.

Fanny Rubio-Moscardo et al., Characterization of 8p21.3 chromosomal deletions in B-cell lymphoma: TRAIL-R1 and TRAIL-R2 as candidate dosage-dependent tumor suppressor genes, Blood, Nov. 1, 2005, vol. 106, No. 9, pp. 3214-3222.

Naoto Itoh et al., The Polypeptide Encoded by the cDNA for Human Cell Surface Antigen Fas Can Mediate Apoptosis, Cell, Jul. 26, 1991, vol. 66, pp. 233-243.

K. L. King and J. A. Cidlowski, Cell Cycle Regulation and Apoptosis, Annual Review of Physiology, 1998, vol. 60, pp. 601-617.

John F. R. Kerr et al., Apoptosis, Its Significance in Cancer and Cancer Therapy, Cancer, Apr. 15, 1994, vol. 73, No. 8, pp. 2013-2028.

Steven R. Wiley et al., Identification and Characterization of a New Member of the TNF Family that Induces Apoptosis, Immunity, Dec. 1995, vol. 3, pp. 673-682.

Robert M. Pitti et al., Induction of Apoptosis by Apo-2 Ligand, a New Member of the Tumor Necrosis Factor Cytokine Family, The Journal of Biological Chemistry, May 31, 1996, vol. 271, No. 22, pp. 12687-12690.

Louis A. Tartaglia and David V. Goeddel, Two TNF Receptors, Immunology Today, 1992, vol. 13, No. 5, pp. 151-153.

Stephen F. Altschul et al., Basic Local Alignment Search Tool, Journal of Molecular Biology, Oct. 5, 1990, vol. 215, No. 3, pp. 403-410.

Stephen F. Altschul et al., Gapped BLAST and PSI-BLAST: a new generation of protein database search programs, Nucleic Acids Research, Sep. 1, 1997, vol. 25, No. 17, pp. 3389-3402.

J. John Cohen, Programmed Cell Death in the Immune System, Advances in Immunology, 1991, vol. 50, pp. 55-85.

Yiehua Zhang, Experimental Study on the Effect of rmhTRAIL in Combination with Dexamethasone, Thalidomide for Nude Mice Bearing RPMI-8226 Cells, Chinese Master's Theses Full-text Database, Medicine and Health Sciences, Oct. 15, 2009, No. 10, pp. E072-92 (partial English translation).

Yiehua Zhang et al., Combined Effect of Recombinant Mutant Human TRAIL and Daunorubicin in Inducing Apoptosis of Leukemia Cell and Its Mechanism, Journal of Experimental Hematology, Dec. 30, 2006, vol. 14, No. 6, pp. 1123-1128 (English Abstract).

European Patent Office Supplementary European Search Report dated Feb. 17, 2015 for European Application No. 11872264.4, 8 pages.

Steven R. Wiley et al., Identification and Characterization of a New Member of the TNF Family that Induces Apoptosis, Immunity, vol. 3, No. 6, Dec. 1, 1995, pp. 673-682.

Robert M. Pitti et al., Induction of Apoptosis by Apo-2 Ligand, a New Member of the Tumor Necrosis Factor Cytokine Family, The Journal of Biological Chemistry, vol. 271, No. 22, May 31, 1996, pp. 12687-12690.

Jin Na Shin et al., Generation of a novel proform of tumor necrosis factor-related apoptosis-inducing ligand (TRAIL) protein that can be reactivated by matrix metalloproteinases, Experimental Cell Research, vol. 312, No. 19, Nov. 15, 2006, pp. 3892-3898.

Chuanying Geng et al., A multicenter, open-label phase II study of recombinant CPT (Circularly Permuted TRAIL) plus thalidomide in patients with relapsed and refractory multiple myeloma, American Journal of Hematology, vol. 89, No. 11, Nov. 2014, pp. 1037-1042.

\* cited by examiner

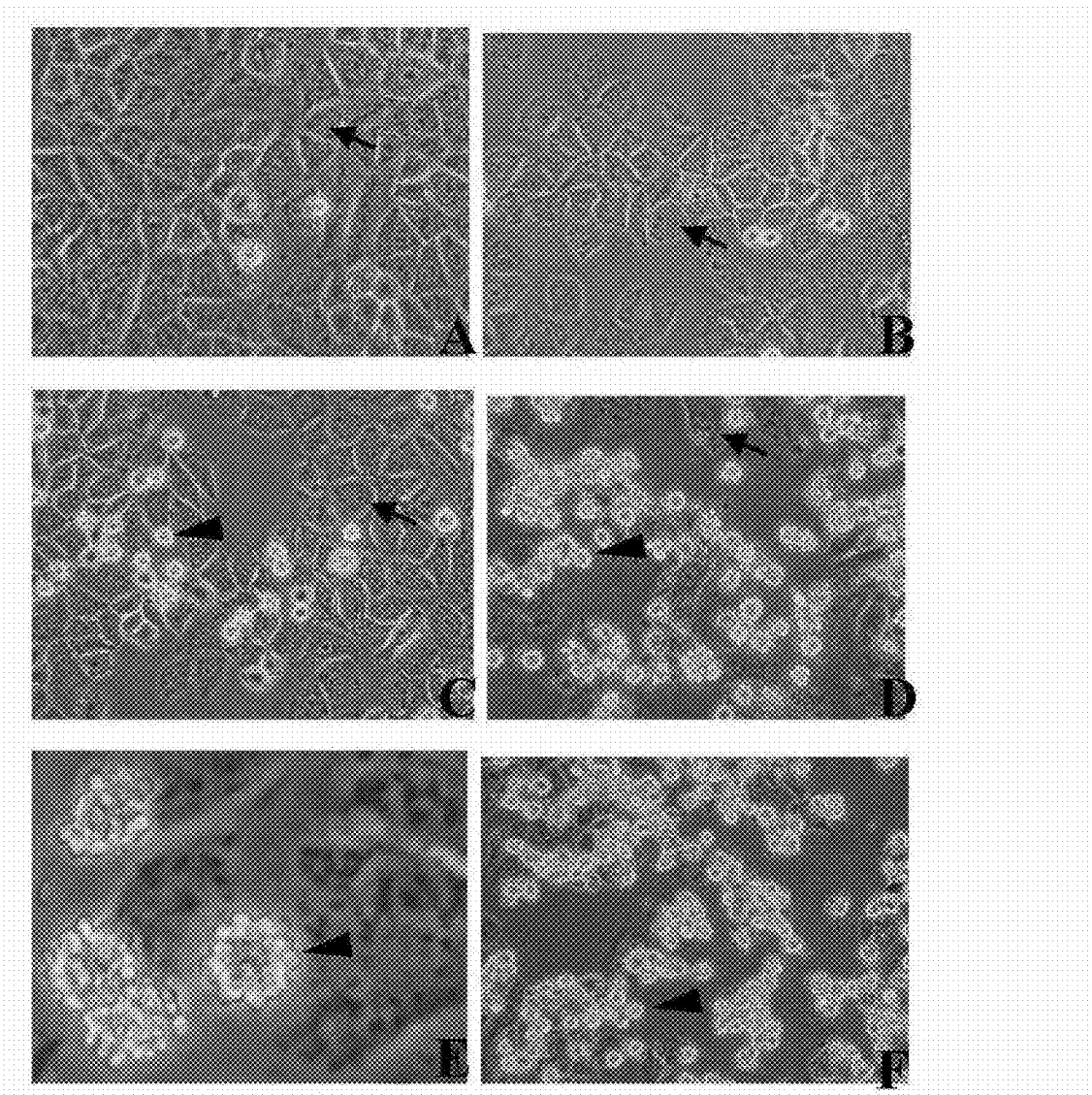
Figure 1 Observation of the killing effect of NCPT-1.M1 on H460 cell under phase contrast microscope.
A: Vehicle control-6h    B: NCPT-1.M1-1h    C: NCPT-1.M1-2h
D: NCPT-1.M1-4h    E: NCPT-1.M1-4h (higher magnification)    F: NCPT-1.M1-6h
▲ represents normal cells    ▲ apoptotic cells: cell budding and blebbing to form apoptotic bodies

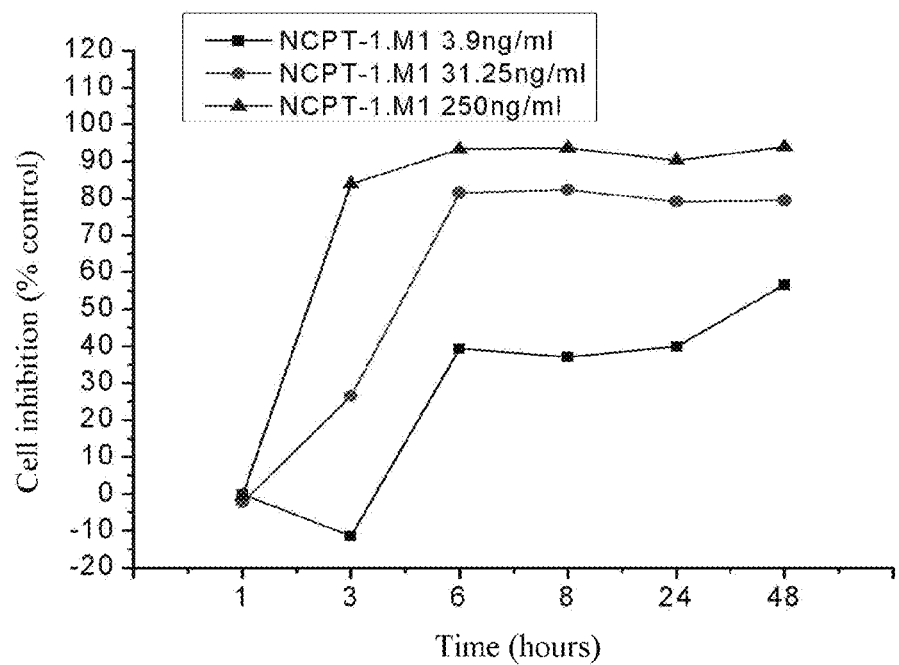
Figure 2 The time-effect relationship of NCPT-1.M1 in killing RPMI8226 cells.

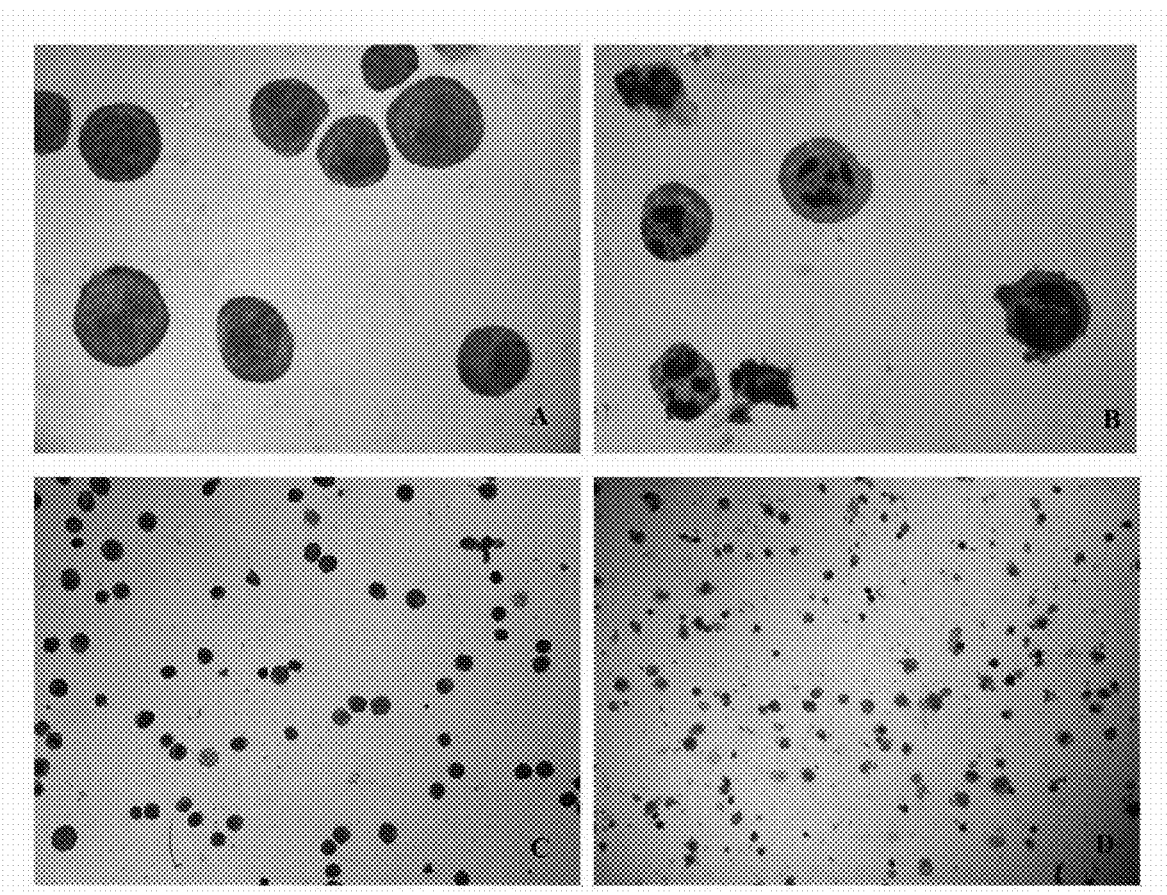
Figure 3 The morphological change of apoptosis of human multiple myeloma cell RPMI 8226 induced by NCPT-1.M1.

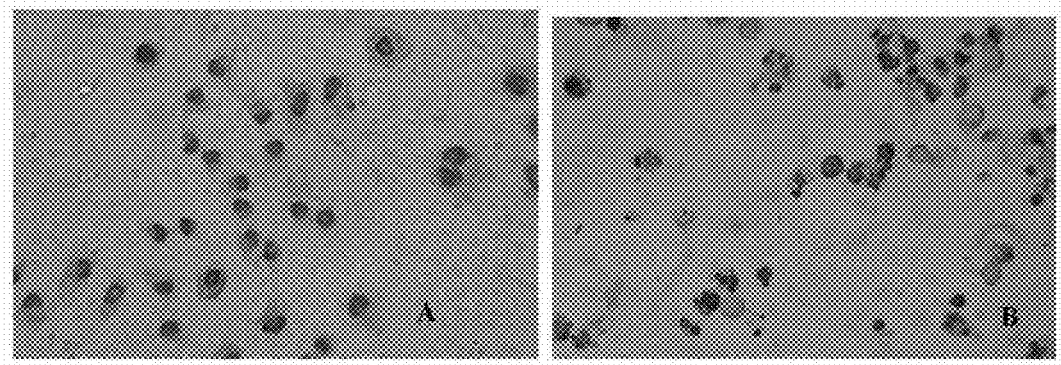
Figure 4 TUNEL assay of apoptosis of human lung cancer NCI-H460 cell line induced by NCPT-1.M1.
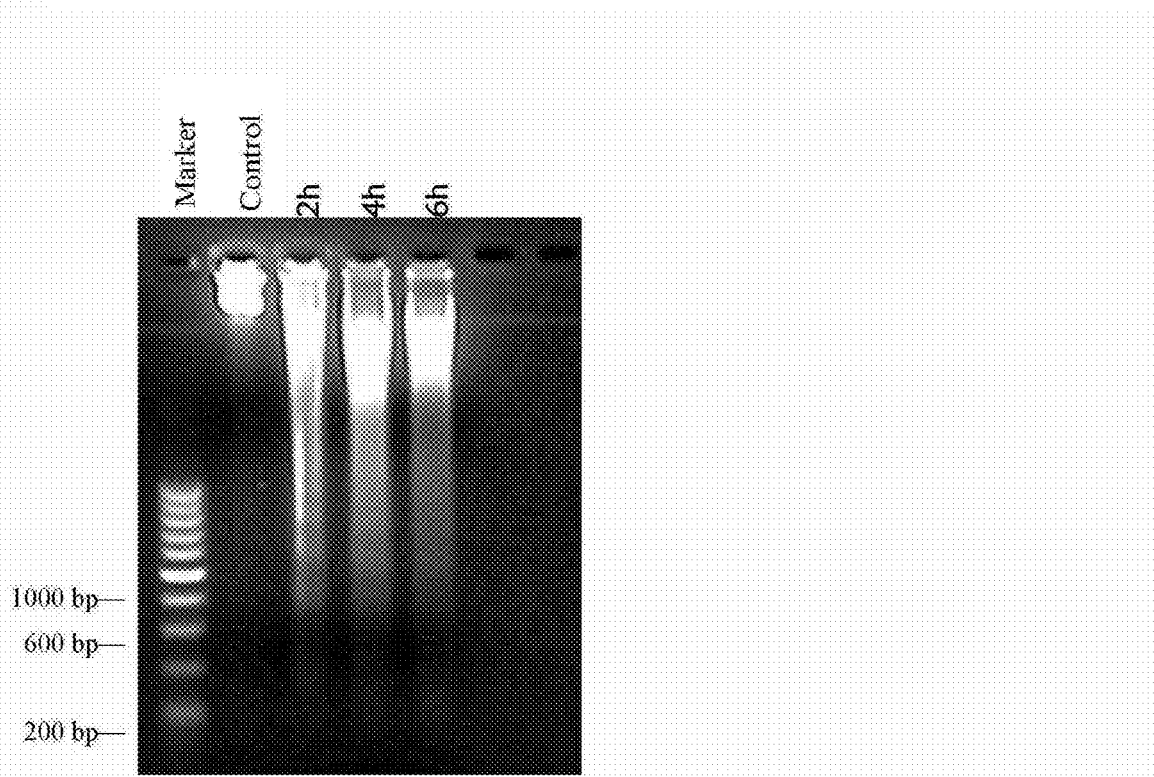
Figure 5 The agarose gel electrophoresis analysis of internucleosomal DNA fragmentation of NCI-H460 cells after incubated with NCPT-1.M1 for varying time.

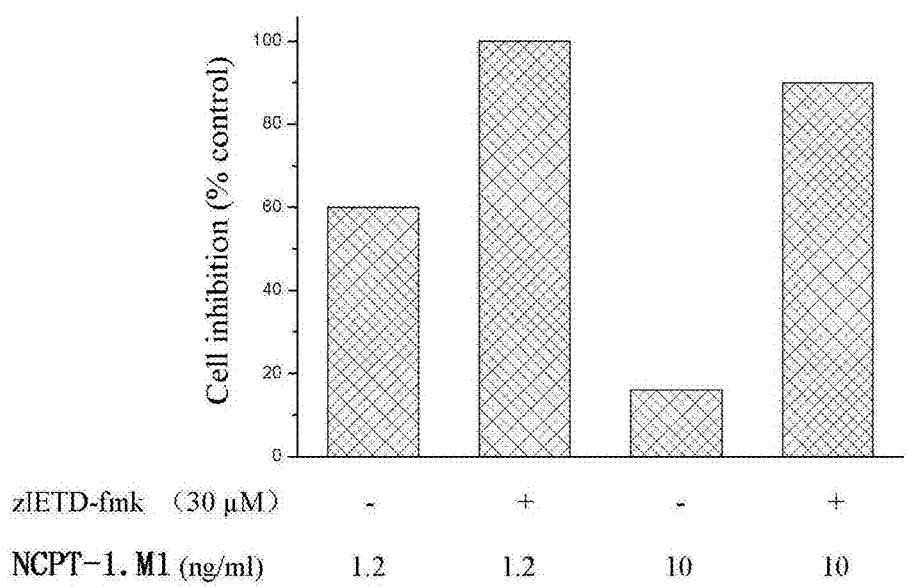
Figure 6 Caspase-8 inhibitor (zIETD-fmk) can inhibit the pro-apoptotic activity of NCPT-1.M1 on H460 cells.

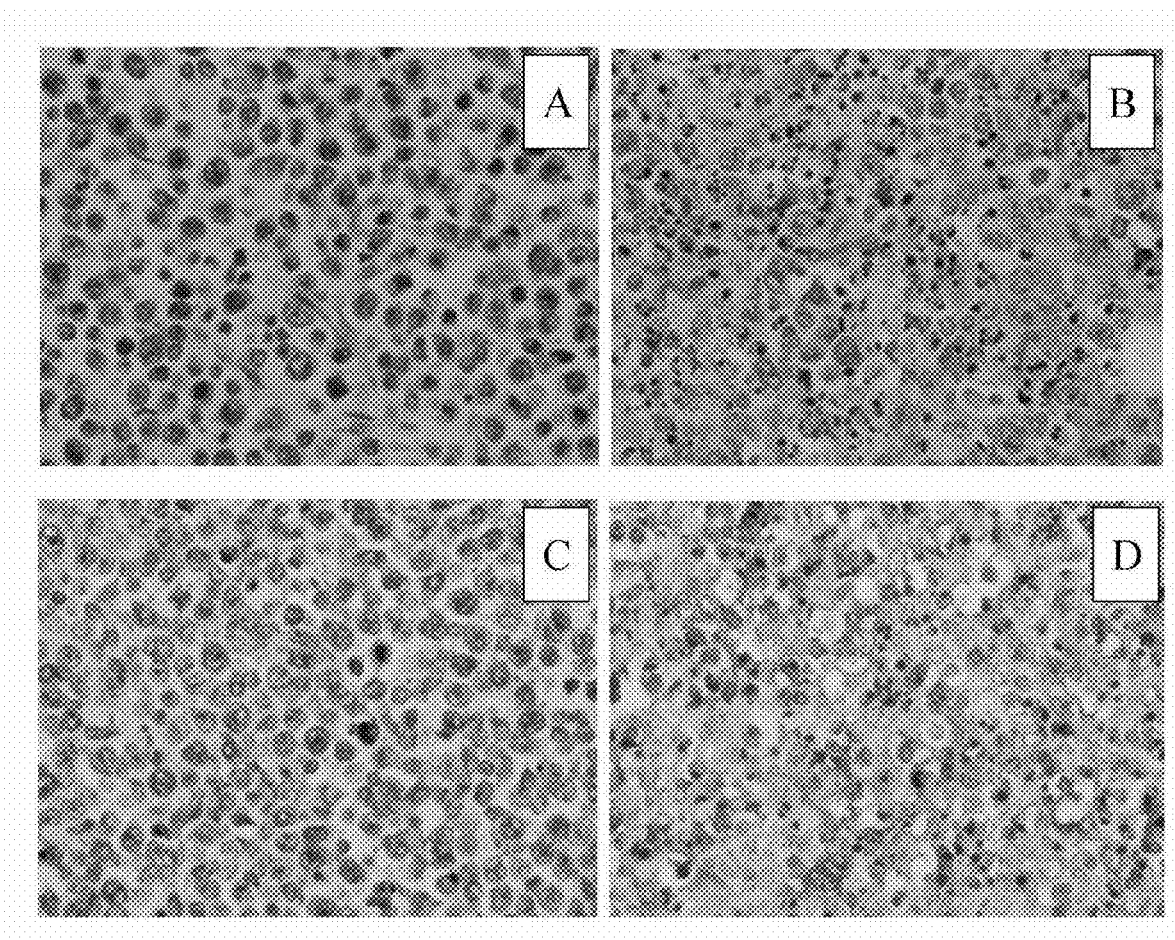
Figure 7 NCPT-1.M1 can result in apoptosis of a large number of tumor cells in tumor tissue

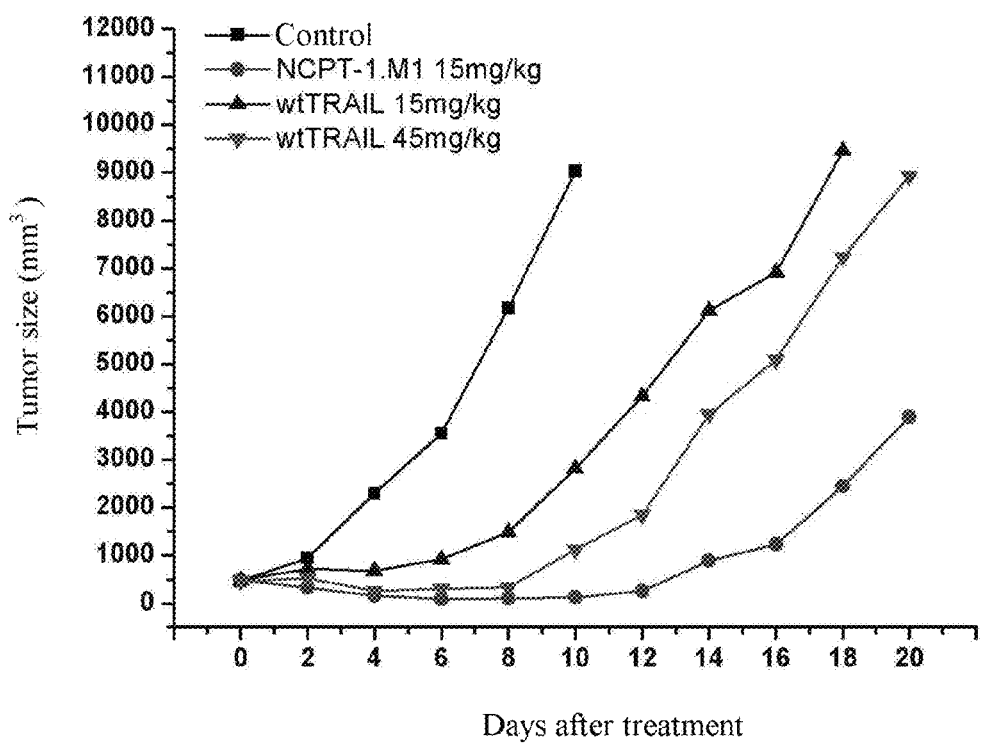
Figure 8 The growth of human RPMI 8226 xenograft tumor in mice is significantly inhibited by NCPT-1.M1.

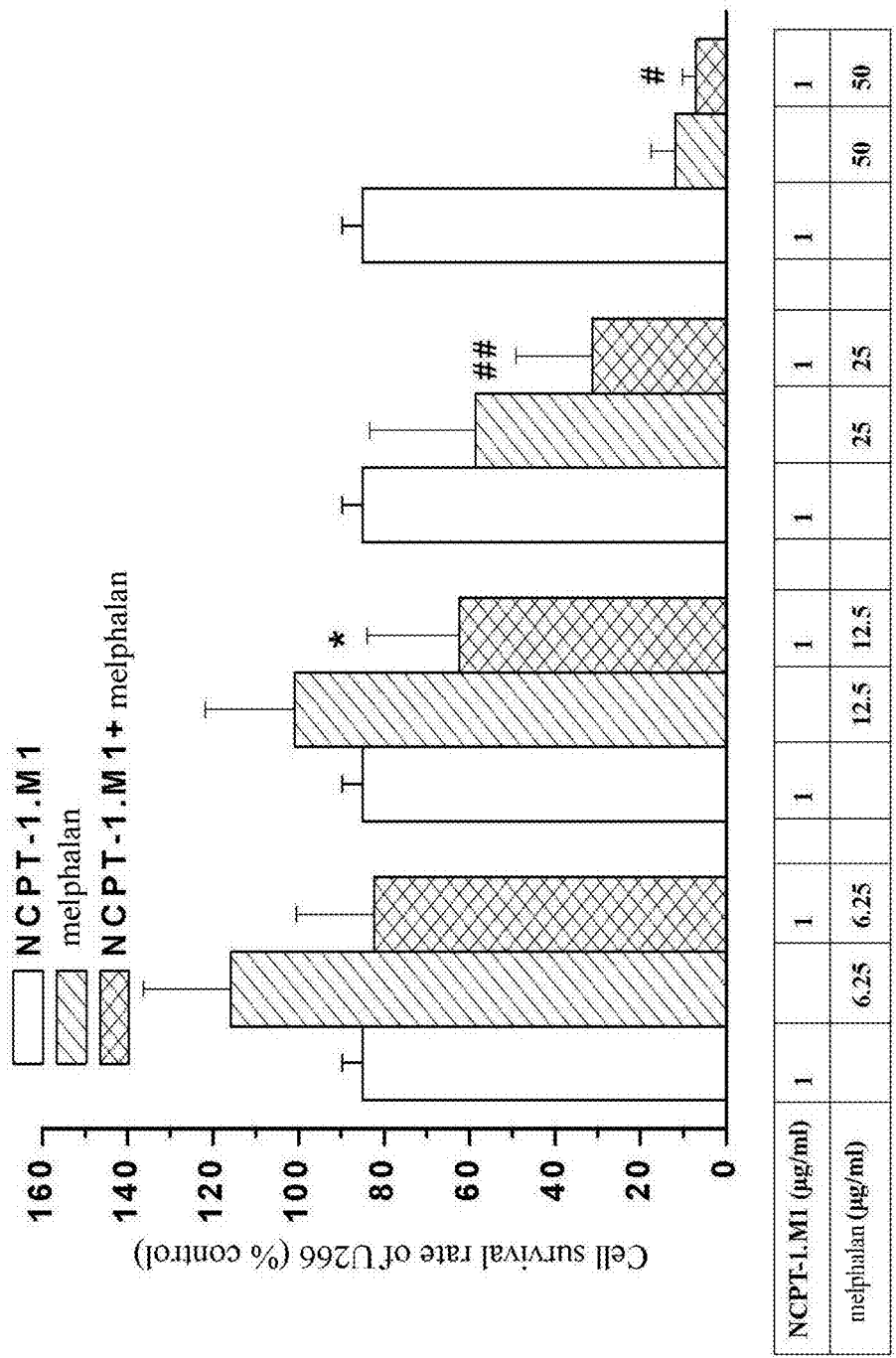
Figure 9 NCPT-1.M1 combined with melphalan can improve the killing effect on human multiple myeloma cell line U266.

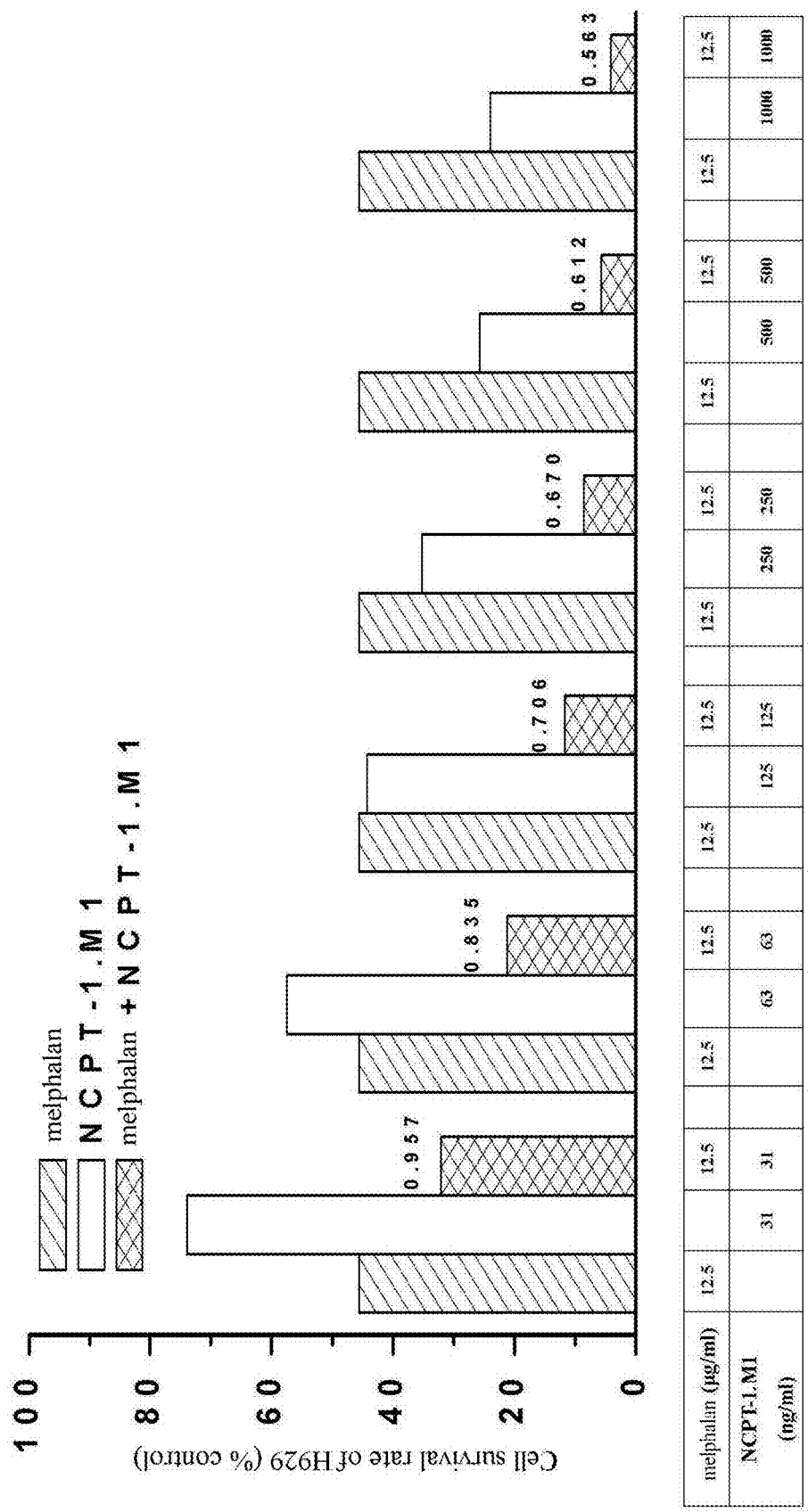
Figure 10 NCPT-1.M1 combined with melphalan has a synergistic killing effect on human MM cell line H929.

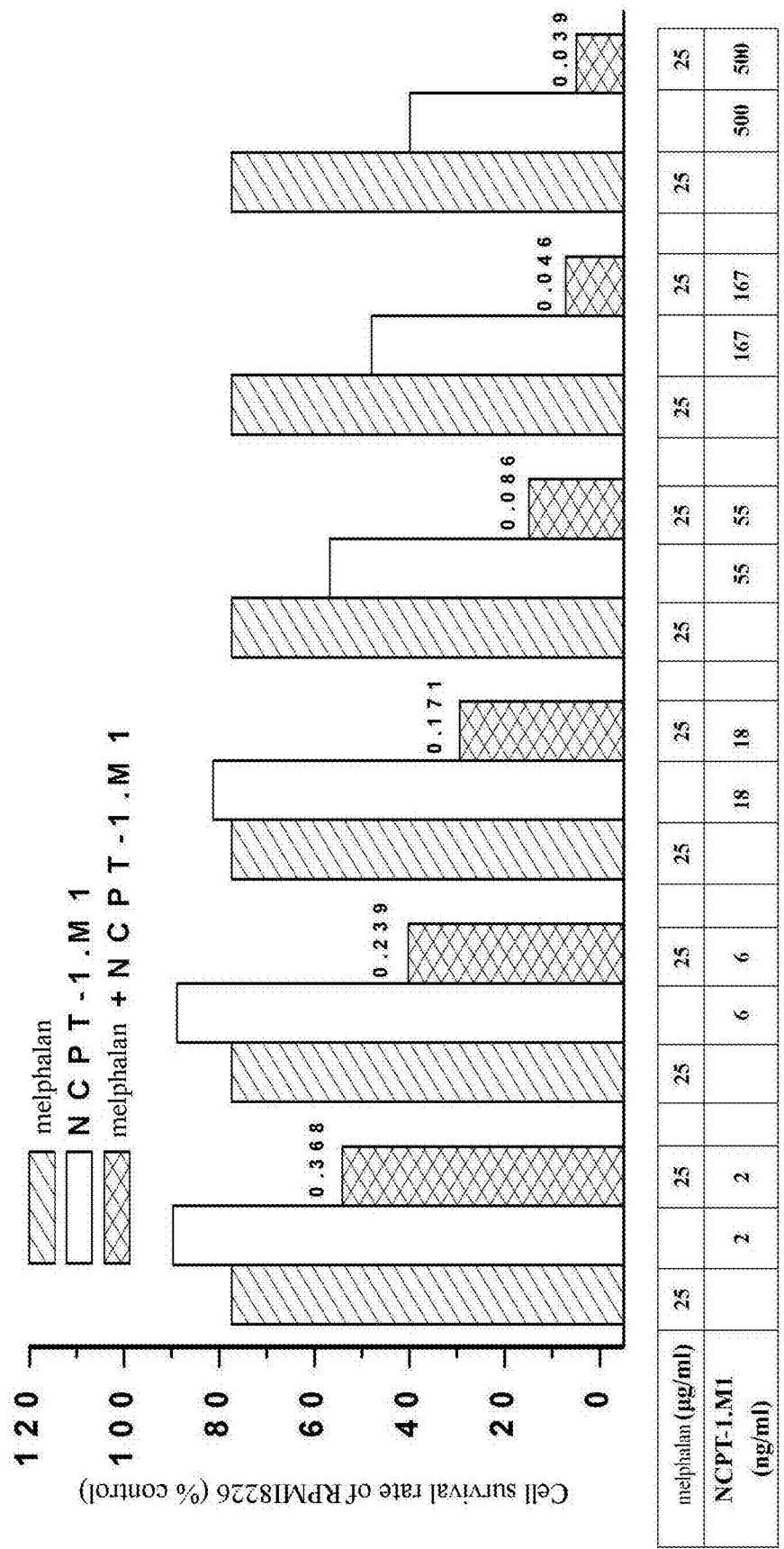
Figure 11 NCPT-1.M1 combined with melphalan has a synergistic killing effect on human MM cell line RPMI8226.

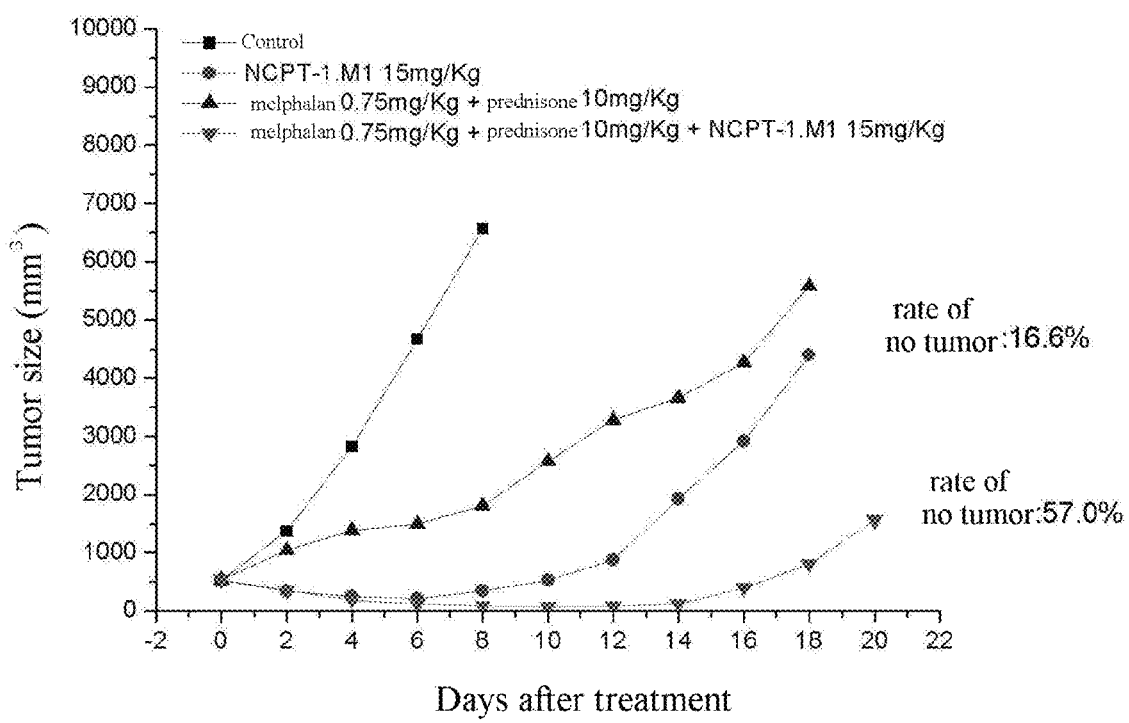
Figure 12 The inhibitory effect of NCPT-1.M1 on the growth of human RPMI8226 xenograft tumor in mice is significantly enhanced by NCPT-1.M1 combined with Melphalan and Prednisone.

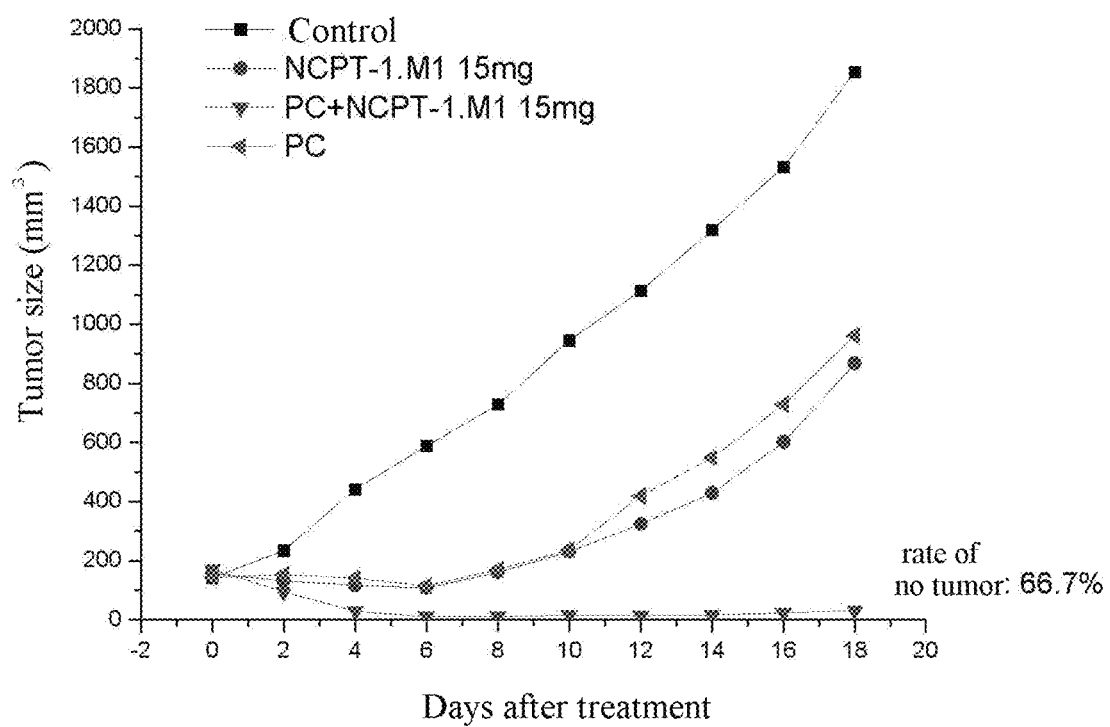
Figure 13 The inhibitory effect of NCPT-1.M1 on the growth of human NCI-H460 xenograft tumor in mice is significantly enhanced by NCPT-1.M1 combined with chemotherapy (PC regimen: paclitaxel plus carboplatin).

SEQUENCE LISTING

<160> NUMBER OF SEQ ID NOS: 48

<210> SEQ ID NO 1
<211> LENGTH: 166
<212> TYPE: PRT
<213> ORGANISM: Artificial sequence
<220> FEATURE:
<223> OTHER INFORMATION: CPT polypeptide sequence

<400> SEQUENCE: 1

Thr Leu Ser Ser Pro Asn Ser Lys Asn Glu Lys Ala Leu Gly Arg Lys
1               5                   10                  15

Ile Asn Ser Trp Glu Ser Ser Arg Ser Gly His Ser Phe Leu Ser Asn
            20                  25                  30

Leu His Leu Arg Asn Gly Glu Leu Val Ile His Glu Lys Gly Phe Tyr
        35                  40                  45

Tyr Ile Tyr Ser Gln Thr Tyr Phe Arg Phe Gln Glu Glu Ile Lys Glu
    50                  55                  60

```
Asn Thr Lys Asn Asp Lys Gln Met Val Gln Tyr Ile Tyr Lys Tyr Thr
 65                  70                  75                  80

Ser Tyr Pro Asp Pro Ile Leu Leu Met Lys Ser Ala Arg Asn Ser Cys
                 85                  90                  95

Trp Ser Lys Asp Ala Glu Tyr Gly Leu Tyr Ser Ile Tyr Gln Gly Gly
                100                 105                 110

Ile Phe Glu Leu Lys Glu Asn Asp Arg Ile Phe Val Ser Val Thr Asn
            115                 120                 125

Glu His Leu Ile Asp Met Asp His Glu Ala Ser Phe Phe Gly Ala Phe
        130                 135                 140

Leu Val Gly Gly Gly Gly Gly Val Ala Ala His Ile Thr Gly Thr
145                 150                 155                 160

Arg Gly Arg Ser Asn Thr
                165

<210> SEQ ID NO 2
<211> LENGTH: 167
<212> TYPE: PRT
<213> ORGANISM: artificial sequence
<220> FEATURE:
<223> OTHER INFORMATION: NCPT-1 polypeptide sequence

<400> SEQUENCE: 2

Thr Leu Ser Ser Pro Asn Ser Lys Asn Glu Lys Ala Leu Gly Arg Lys
  1               5                  10                  15

Ile Asn Ser Trp Glu Ser Ser Arg Ser Gly His Ser Phe Leu Ser Asn
             20                  25                  30

Leu His Leu Arg Asn Gly Glu Leu Val Ile His Glu Lys Gly Phe Tyr
         35                  40                  45

Tyr Ile Tyr Ser Gln Thr Tyr Phe Arg Phe Gln Glu Glu Ile Lys Glu
     50                  55                  60

Asn Thr Lys Asn Asp Lys Gln Met Val Gln Tyr Ile Tyr Lys Tyr Thr
 65                  70                  75                  80

Ser Tyr Pro Asp Pro Ile Leu Leu Met Lys Ser Ala Arg Asn Ser Cys
                 85                  90                  95

Trp Ser Lys Asp Ala Glu Tyr Gly Leu Tyr Ser Ile Tyr Gln Gly Gly
                100                 105                 110

Ile Phe Glu Leu Lys Glu Asn Asp Arg Ile Phe Val Ser Val Thr Asn
            115                 120                 125

Glu His Leu Ile Asp Met Asp His Glu Ala Ser Phe Phe Gly Ala Phe
        130                 135                 140

Leu Val Gly Gly Gly Gly Gly Arg Val Ala Ala His Ile Thr Gly
145                 150                 155                 160

Thr Arg Gly Arg Ser Asn Thr
                165

<210> SEQ ID NO 3
<211> LENGTH: 193
<212> TYPE: PRT
<213> ORGANISM: artificial sequence
<220> FEATURE:
<223> OTHER INFORMATION: NCPT-2 polypeptide sequence

<400> SEQUENCE: 3

Thr Leu Ser Ser Pro Asn Ser Lys Asn Glu Lys Ala Leu Gly Arg Lys
  1               5                  10                  15

Ile Asn Ser Trp Glu Ser Ser Arg Ser Gly His Ser Phe Leu Ser Asn
             20                  25                  30
```

Leu His Leu Arg Asn Gly Glu Leu Val Ile His Glu Lys Gly Phe Tyr
            35                  40                  45

Tyr Ile Tyr Ser Gln Thr Tyr Phe Arg Phe Gln Glu Glu Ile Lys Glu
        50                  55                  60

Asn Thr Lys Asn Asp Lys Gln Met Val Gln Tyr Ile Tyr Lys Tyr Thr
65                  70                  75                  80

Ser Tyr Pro Asp Pro Ile Leu Leu Met Lys Ser Ala Arg Asn Ser Cys
                85                  90                  95

Trp Ser Lys Asp Ala Glu Tyr Gly Leu Tyr Ser Ile Tyr Gln Gly Gly
                100                 105                 110

Ile Phe Glu Leu Lys Glu Asn Asp Arg Ile Phe Val Ser Val Thr Asn
                115                 120                 125

Glu His Leu Ile Asp Met Asp His Glu Ala Ser Phe Phe Gly Ala Phe
            130                 135                 140

Leu Val Gly Gly Gly Gly Gly Thr Ser Glu Glu Thr Ile Ser Thr
145                 150                 155                 160

Val Gln Glu Lys Gln Gln Asn Ile Ser Pro Leu Val Arg Glu Arg Gly
                    165                 170                 175

Pro Gln Arg Val Ala Ala His Ile Thr Gly Thr Arg Gly Arg Ser Asn
                180                 185                 190

Thr

<210> SEQ ID NO 4
<211> LENGTH: 174
<212> TYPE: PRT
<213> ORGANISM: artificial sequence
<220> FEATURE:
<223> OTHER INFORMATION: NCPT-3 polypeptide sequence

<400> SEQUENCE: 4

Thr Leu Ser Ser Pro Asn Ser Lys Asn Glu Lys Ala Leu Gly Arg Lys
1               5                   10                  15

Ile Asn Ser Trp Glu Ser Ser Arg Ser Gly His Ser Phe Leu Ser Asn
                20                  25                  30

Leu His Leu Arg Asn Gly Glu Leu Val Ile His Glu Lys Gly Phe Tyr
            35                  40                  45

Tyr Ile Tyr Ser Gln Thr Tyr Phe Arg Phe Gln Glu Glu Ile Lys Glu
        50                  55                  60

Asn Thr Lys Asn Asp Lys Gln Met Val Gln Tyr Ile Tyr Lys Tyr Thr
65                  70                  75                  80

Ser Tyr Pro Asp Pro Ile Leu Leu Met Lys Ser Ala Arg Asn Ser Cys
                85                  90                  95

Trp Ser Lys Asp Ala Glu Tyr Gly Leu Tyr Ser Ile Tyr Gln Gly Gly
                100                 105                 110

Ile Phe Glu Leu Lys Glu Asn Asp Arg Ile Phe Val Ser Val Thr Asn
                115                 120                 125

Glu His Leu Ile Asp Met Asp His Glu Ala Ser Phe Phe Gly Ala Phe
            130                 135                 140

Leu Val Gly Gly Gly Gly Gly Val Arg Glu Arg Gly Pro Gln Arg
145                 150                 155                 160

Val Ala Ala His Ile Thr Gly Thr Arg Gly Arg Ser Asn Thr
                    165                 170

<210> SEQ ID NO 5
<211> LENGTH: 175

<212> TYPE: PRT
<213> ORGANISM: artificial sequence
<220> FEATURE:
<223> OTHER INFORMATION: NCPT-1.M1 polypeptide sequence

<400> SEQUENCE: 5

```
Met Gly His His His His His Thr Leu Ser Ser Pro Asn Ser Lys
1               5                   10                  15

Asn Glu Lys Ala Leu Gly Arg Lys Ile Asn Ser Trp Glu Ser Ser Arg
            20                  25                  30

Ser Gly His Ser Phe Leu Ser Asn Leu His Leu Arg Asn Gly Glu Leu
        35                  40                  45

Val Ile His Glu Lys Gly Phe Tyr Tyr Ile Tyr Ser Gln Thr Tyr Phe
    50                  55                  60

Arg Phe Gln Glu Glu Ile Lys Glu Asn Thr Lys Asn Asp Lys Gln Met
65                  70                  75                  80

Val Gln Tyr Ile Tyr Lys Tyr Thr Ser Tyr Pro Asp Pro Ile Leu Leu
                85                  90                  95

Met Lys Ser Ala Arg Asn Ser Cys Trp Ser Lys Asp Ala Glu Tyr Gly
            100                 105                 110

Leu Tyr Ser Ile Tyr Gln Gly Gly Ile Phe Glu Leu Lys Glu Asn Asp
        115                 120                 125

Arg Ile Phe Val Ser Val Thr Asn Glu His Leu Ile Asp Met Asp His
    130                 135                 140

Glu Ala Ser Phe Phe Gly Ala Phe Leu Val Gly Gly Gly Gly Gly
145                 150                 155                 160

Arg Val Ala Ala His Ile Thr Gly Thr Arg Gly Arg Ser Asn Thr
                165                 170                 175
```

<210> SEQ ID NO 6
<211> LENGTH: 175
<212> TYPE: PRT
<213> ORGANISM: artificial sequence
<220> FEATURE:
<223> OTHER INFORMATION: NCPT-1.M2 polypeptide sequence

<400> SEQUENCE: 6

```
Met Gly Thr Leu Ser Ser Pro Asn Ser Lys Asn Glu Lys Ala Leu Gly
1               5                   10                  15

Arg Lys Ile Asn Ser Trp Glu Ser Ser Arg Ser Gly His Ser Phe Leu
            20                  25                  30

Ser Asn Leu His Leu Arg Asn Gly Glu Leu Val Ile His Glu Lys Gly
        35                  40                  45

Phe Tyr Tyr Ile Tyr Ser Gln Thr Tyr Phe Arg Phe Gln Glu Glu Ile
    50                  55                  60

Lys Glu Asn Thr Lys Asn Asp Lys Gln Met Val Gln Tyr Ile Tyr Lys
65                  70                  75                  80

Tyr Thr Ser Tyr Pro Asp Pro Ile Leu Leu Met Lys Ser Ala Arg Asn
                85                  90                  95

Ser Cys Trp Ser Lys Asp Ala Glu Tyr Gly Leu Tyr Ser Ile Tyr Gln
            100                 105                 110

Gly Gly Ile Phe Glu Leu Lys Glu Asn Asp Arg Ile Phe Val Ser Val
        115                 120                 125

Thr Asn Glu His Leu Ile Asp Met Asp His Glu Ala Ser Phe Phe Gly
    130                 135                 140

Ala Phe Leu Val Gly Gly Gly Gly Gly Gly Arg Val Ala Ala His Ile
145                 150                 155                 160
```

```
Thr Gly Thr Arg Gly Arg Ser Asn Thr His His His His His
                165                 170                 175

<210> SEQ ID NO 7
<211> LENGTH: 172
<212> TYPE: PRT
<213> ORGANISM: artificial sequence
<220> FEATURE:
<223> OTHER INFORMATION: NCPT-1.M3 polypeptide sequence

<400> SEQUENCE: 7

Met Gly His His His Thr Leu Ser Ser Pro Asn Ser Lys Asn Glu Lys
1               5                   10                  15

Ala Leu Gly Arg Lys Ile Asn Ser Trp Glu Ser Ser Arg Ser Gly His
                20                  25                  30

Ser Phe Leu Ser Asn Leu His Leu Arg Asn Gly Glu Leu Val Ile His
            35                  40                  45

Glu Lys Gly Phe Tyr Tyr Ile Tyr Ser Gln Thr Tyr Phe Arg Phe Gln
50                  55                  60

Glu Glu Ile Lys Glu Asn Thr Lys Asn Asp Lys Gln Met Val Gln Tyr
65                  70                  75                  80

Ile Tyr Lys Tyr Thr Ser Tyr Pro Asp Pro Ile Leu Leu Met Lys Ser
                85                  90                  95

Ala Arg Asn Ser Cys Trp Ser Lys Asp Ala Glu Tyr Gly Leu Tyr Ser
            100                 105                 110

Ile Tyr Gln Gly Gly Ile Phe Glu Leu Lys Glu Asn Asp Arg Ile Phe
        115                 120                 125

Val Ser Val Thr Asn Glu His Leu Ile Asp Met Asp His Glu Ala Ser
    130                 135                 140

Phe Phe Gly Ala Phe Leu Val Gly Gly Gly Gly Arg Val Ala
145                 150                 155                 160

Ala His Ile Thr Gly Thr Arg Gly Arg Ser Asn Thr
                165                 170

<210> SEQ ID NO 8
<211> LENGTH: 173
<212> TYPE: PRT
<213> ORGANISM: artificial sequence
<220> FEATURE:
<223> OTHER INFORMATION: NCPT-1.M4 polypeptide sequence

<400> SEQUENCE: 8

His His His His His Thr Leu Ser Ser Pro Asn Ser Lys Asn Glu
1               5                   10                  15

Lys Ala Leu Gly Arg Lys Ile Asn Ser Trp Glu Ser Ser Arg Ser Gly
                20                  25                  30

His Ser Phe Leu Ser Asn Leu His Leu Arg Asn Gly Glu Leu Val Ile
            35                  40                  45

His Glu Lys Gly Phe Tyr Tyr Ile Tyr Ser Gln Thr Tyr Phe Arg Phe
        50                  55                  60

Gln Glu Glu Ile Lys Glu Asn Thr Lys Asn Asp Lys Gln Met Val Gln
65                  70                  75                  80

Tyr Ile Tyr Lys Tyr Thr Ser Tyr Pro Asp Pro Ile Leu Leu Met Lys
                85                  90                  95

Ser Ala Arg Asn Ser Cys Trp Ser Lys Asp Ala Glu Tyr Gly Leu Tyr
            100                 105                 110

Ser Ile Tyr Gln Gly Gly Ile Phe Glu Leu Lys Glu Asn Asp Arg Ile
```

```
            115                 120                 125
Phe Val Ser Val Thr Asn Glu His Leu Ile Asp Met Asp His Glu Ala
        130                 135                 140
Ser Phe Phe Gly Ala Phe Leu Val Gly Gly Gly Gly Gly Arg Val
145                 150                 155                 160
Ala Ala His Ile Thr Gly Thr Arg Gly Arg Ser Asn Thr
                165                 170

<210> SEQ ID NO 9
<211> LENGTH: 175
<212> TYPE: PRT
<213> ORGANISM: artificial sequence
<220> FEATURE:
<223> OTHER INFORMATION: NCPT-1.M5 polypeptide sequence

<400> SEQUENCE: 9

Met Gly His His His His His His Thr Leu Ser Ser Pro Asn Ser Lys
1               5                   10                  15
Asn Glu Lys Ala Leu Gly Arg Lys Ile Asn Ser Trp Glu Ser Ser Arg
            20                  25                  30
Ser Gly His Ser Phe Leu Ser Asn Leu His Leu Arg Asn Gly Glu Leu
        35                  40                  45
Val Ile His Glu Lys Gly Phe Tyr Tyr Ile Tyr Ser Gln Thr Tyr Phe
    50                  55                  60
Arg Phe Gln Glu Glu Ile Lys Glu Asn Thr Lys Asn Asp Lys Gln Met
65                  70                  75                  80
Val Gln Tyr Ile Tyr Lys Tyr Thr Ser Tyr Pro Asp Pro Ile Leu Leu
                85                  90                  95
Met Lys Ser Ala Arg Asn Ser Cys Trp Ser Lys Asp Ala Glu Tyr Gly
            100                 105                 110
Leu Tyr Ser Ile Tyr Gln Gly Gly Ile Phe Glu Leu Lys Glu Asn Asp
        115                 120                 125
Arg Ile Phe Val Ser Val Thr Asn Glu His Leu Ile Asp Met Asp His
    130                 135                 140
Glu Ala Ser Phe Phe Gly Ala Phe Leu Val Gly Gly Ser Gly Gly Gly
145                 150                 155                 160
Arg Val Ala Ala His Ile Thr Gly Thr Arg Gly Arg Ser Asn Thr
                165                 170                 175

<210> SEQ ID NO 10
<211> LENGTH: 177
<212> TYPE: PRT
<213> ORGANISM: artificial sequence
<220> FEATURE:
<223> OTHER INFORMATION: NCPT-1.M6 polypeptide sequence

<400> SEQUENCE: 10

Met Gly His His His His His His Thr Leu Ser Ser Pro Asn Ser Lys
1               5                   10                  15
Asn Glu Lys Ala Leu Gly Arg Lys Ile Asn Ser Trp Glu Ser Ser Arg
            20                  25                  30
Ser Gly His Ser Phe Leu Ser Asn Leu His Leu Arg Asn Gly Glu Leu
        35                  40                  45
Val Ile His Glu Lys Gly Phe Tyr Tyr Ile Tyr Ser Gln Thr Tyr Phe
    50                  55                  60
Arg Phe Gln Glu Glu Ile Lys Glu Asn Thr Lys Asn Asp Lys Gln Met
65                  70                  75                  80
```

```
Val Gln Tyr Ile Tyr Lys Tyr Thr Ser Tyr Pro Asp Pro Ile Leu Leu
                85                  90                  95

Met Lys Ser Ala Arg Asn Ser Cys Trp Ser Lys Asp Ala Glu Tyr Gly
            100                 105                 110

Leu Tyr Ser Ile Tyr Gln Gly Gly Ile Phe Glu Leu Lys Glu Asn Asp
        115                 120                 125

Arg Ile Phe Val Ser Val Thr Asn Glu His Leu Ile Asp Met Asp His
    130                 135                 140

Glu Ala Ser Phe Phe Gly Ala Phe Leu Val Gly Gly Ser Gly Gly
145                 150                 155                 160

Gly Gly Arg Val Ala Ala His Ile Thr Gly Thr Arg Gly Arg Ser Asn
            165                 170                 175

Thr

<210> SEQ ID NO 11
<211> LENGTH: 178
<212> TYPE: PRT
<213> ORGANISM: artificial sequence
<220> FEATURE:
<223> OTHER INFORMATION: NCPT-1.M7 polypeptide sequence

<400> SEQUENCE: 11

Met Gly His His His His His His His Thr Leu Ser Ser Pro
1               5                   10                  15

Asn Ser Lys Asn Glu Lys Ala Leu Gly Arg Lys Ile Asn Ser Trp Glu
            20                  25                  30

Ser Ser Arg Ser Gly His Ser Phe Leu Ser Asn Leu His Leu Arg Asn
        35                  40                  45

Gly Glu Leu Val Ile His Glu Lys Gly Phe Tyr Tyr Ile Tyr Ser Gln
    50                  55                  60

Thr Tyr Phe Arg Phe Gln Glu Ile Lys Glu Asn Thr Lys Asn Asp
65                  70                  75                  80

Lys Gln Met Val Gln Tyr Ile Tyr Lys Tyr Thr Ser Tyr Pro Asp Pro
                85                  90                  95

Ile Leu Leu Met Lys Ser Ala Arg Asn Ser Cys Trp Ser Lys Asp Ala
            100                 105                 110

Glu Tyr Gly Leu Tyr Ser Ile Tyr Gln Gly Gly Ile Phe Glu Leu Lys
        115                 120                 125

Glu Asn Asp Arg Ile Phe Val Ser Val Thr Asn Glu His Leu Ile Asp
    130                 135                 140

Met Asp His Glu Ala Ser Phe Phe Gly Ala Phe Leu Val Gly Gly Gly
145                 150                 155                 160

Gly Gly Gly Arg Val Ala Ala His Ile Thr Gly Thr Arg Gly Arg Ser
            165                 170                 175

Asn Thr

<210> SEQ ID NO 12
<211> LENGTH: 175
<212> TYPE: PRT
<213> ORGANISM: artificial sequence
<220> FEATURE:
<223> OTHER INFORMATION: NCPT-1.M8 polypeptide sequence

<400> SEQUENCE: 12

Met Gly Thr Arg Gly Arg Ser Asn Thr Leu Ser Ser Pro Asn Ser Lys
1               5                   10                  15

Asn Glu Lys Ala Leu Gly Arg Lys Ile Asn Ser Trp Glu Ser Ser Arg
```

```
            20                  25                  30
Ser Gly His Ser Phe Leu Ser Asn Leu His Leu Arg Asn Gly Glu Leu
            35                  40                  45

Val Ile His Glu Lys Gly Phe Tyr Tyr Ile Tyr Ser Gln Thr Tyr Phe
        50                  55                  60

Arg Phe Gln Glu Glu Ile Lys Glu Asn Thr Lys Asn Asp Lys Gln Met
65                  70                  75                  80

Val Gln Tyr Ile Tyr Lys Tyr Thr Ser Tyr Pro Asp Pro Ile Leu Leu
                85                  90                  95

Met Lys Ser Ala Arg Asn Ser Cys Trp Ser Lys Asp Ala Glu Tyr Gly
            100                 105                 110

Leu Tyr Ser Ile Tyr Gln Gly Gly Ile Phe Glu Leu Lys Glu Asn Asp
        115                 120                 125

Arg Ile Phe Val Ser Val Thr Asn Glu His Leu Ile Asp Met Asp His
    130                 135                 140

Glu Ala Ser Phe Phe Gly Ala Phe Leu Val Gly Gly Gly Gly Gly Gly
145                 150                 155                 160

Arg Val Ala Ala His Ile Thr Gly Thr Arg Gly Arg Ser Asn Thr
                165                 170                 175

<210> SEQ ID NO 13
<211> LENGTH: 175
<212> TYPE: PRT
<213> ORGANISM: artificial sequence
<220> FEATURE:
<223> OTHER INFORMATION: NCPT-1.M9 polypeptide sequence

<400> SEQUENCE: 13

Met Gly Asn Asn Asn Asn Asn Thr Leu Ser Ser Pro Asn Ser Lys
1               5                   10                  15

Asn Glu Lys Ala Leu Gly Arg Lys Ile Asn Ser Trp Glu Ser Ser Arg
            20                  25                  30

Ser Gly His Ser Phe Leu Ser Asn Leu His Leu Arg Asn Gly Glu Leu
            35                  40                  45

Val Ile His Glu Lys Gly Phe Tyr Tyr Ile Tyr Ser Gln Thr Tyr Phe
        50                  55                  60

Arg Phe Gln Glu Glu Ile Lys Glu Asn Thr Lys Asn Asp Lys Gln Met
65                  70                  75                  80

Val Gln Tyr Ile Tyr Lys Tyr Thr Ser Tyr Pro Asp Pro Ile Leu Leu
                85                  90                  95

Met Lys Ser Ala Arg Asn Ser Cys Trp Ser Lys Asp Ala Glu Tyr Gly
            100                 105                 110

Leu Tyr Ser Ile Tyr Gln Gly Gly Ile Phe Glu Leu Lys Glu Asn Asp
        115                 120                 125

Arg Ile Phe Val Ser Val Thr Asn Glu His Leu Ile Asp Met Asp His
    130                 135                 140

Glu Ala Ser Phe Phe Gly Ala Phe Leu Val Gly Gly Gly Gly Gly Gly
145                 150                 155                 160

Arg Val Ala Ala His Ile Thr Gly Thr Arg Gly Arg Ser Asn Thr
                165                 170                 175

<210> SEQ ID NO 14
<211> LENGTH: 175
<212> TYPE: PRT
<213> ORGANISM: artificial sequence
<220> FEATURE:
<223> OTHER INFORMATION: NCPT-1.M10 polypeptide sequence
```

<400> SEQUENCE: 14

Met Gly Thr Leu Ser Ser Pro Asn Ser Lys Asn Glu Lys Ala Leu Gly
1               5                   10                  15

Arg Lys Ile Asn Ser Trp Glu Ser Ser Arg Ser Gly His Ser Phe Leu
            20                  25                  30

Ser Asn Leu His Leu Arg Asn Gly Glu Leu Val Ile His Glu Lys Gly
        35                  40                  45

Phe Tyr Tyr Ile Tyr Ser Gln Thr Tyr Phe Arg Phe Gln Glu Glu Ile
    50                  55                  60

Lys Glu Asn Thr Lys Asn Asp Lys Gln Met Val Gln Tyr Ile Tyr Lys
65                  70                  75                  80

Tyr Thr Ser Tyr Pro Asp Pro Ile Leu Leu Met Lys Ser Ala Arg Asn
                85                  90                  95

Ser Cys Trp Ser Lys Asp Ala Glu Tyr Gly Leu Tyr Ser Ile Tyr Gln
            100                 105                 110

Gly Gly Ile Phe Glu Leu Lys Glu Asn Asp Arg Ile Phe Val Ser Val
        115                 120                 125

Thr Asn Glu His Leu Ile Asp Met Asp His Glu Ala Ser Phe Phe Gly
130                 135                 140

Ala Phe Leu Val Gly Gly Gly Gly Gly Arg Val Ala Ala His Ile
145                 150                 155                 160

Thr Gly Thr Arg Gly Arg Ser Asn Thr Leu Ser Ser Pro Asn Ser
                165                 170                 175

<210> SEQ ID NO 15
<211> LENGTH: 201
<212> TYPE: PRT
<213> ORGANISM: artificial sequence
<220> FEATURE:
<223> OTHER INFORMATION: NCPT-2.M11 polypeptide sequence

<400> SEQUENCE: 15

Met Gly His His His His His His Thr Leu Ser Ser Pro Asn Ser Lys
1               5                   10                  15

Asn Glu Lys Ala Leu Gly Arg Lys Ile Asn Ser Trp Glu Ser Ser Arg
            20                  25                  30

Ser Gly His Ser Phe Leu Ser Asn Leu His Leu Arg Asn Gly Glu Leu
        35                  40                  45

Val Ile His Glu Lys Gly Phe Tyr Tyr Ile Tyr Ser Gln Thr Tyr Phe
    50                  55                  60

Arg Phe Gln Glu Glu Ile Lys Glu Asn Thr Lys Asn Asp Lys Gln Met
65                  70                  75                  80

Val Gln Tyr Ile Tyr Lys Tyr Thr Ser Tyr Pro Asp Pro Ile Leu Leu
                85                  90                  95

Met Lys Ser Ala Arg Asn Ser Cys Trp Ser Lys Asp Ala Glu Tyr Gly
            100                 105                 110

Leu Tyr Ser Ile Tyr Gln Gly Gly Ile Phe Glu Leu Lys Glu Asn Asp
        115                 120                 125

Arg Ile Phe Val Ser Val Thr Asn Glu His Leu Ile Asp Met Asp His
130                 135                 140

Glu Ala Ser Phe Phe Gly Ala Phe Leu Val Gly Gly Gly Gly Gly
145                 150                 155                 160

Thr Ser Glu Glu Thr Ile Ser Thr Val Gln Lys Gln Gln Asn Ile
                165                 170                 175

Ser Pro Leu Val Arg Glu Arg Gly Pro Gln Arg Val Ala Ala His Ile
        180                 185                 190

Thr Gly Thr Arg Gly Arg Ser Asn Thr
        195                 200

<210> SEQ ID NO 16
<211> LENGTH: 182
<212> TYPE: PRT
<213> ORGANISM: artificial sequence
<220> FEATURE:
<223> OTHER INFORMATION: NCPT-3.M12 polypeptide sequence

<400> SEQUENCE: 16

Met Gly His His His His His Thr Leu Ser Ser Pro Asn Ser Lys
1               5                   10                  15

Asn Glu Lys Ala Leu Gly Arg Lys Ile Asn Ser Trp Glu Ser Ser Arg
            20                  25                  30

Ser Gly His Ser Phe Leu Ser Asn Leu His Leu Arg Asn Gly Glu Leu
        35                  40                  45

Val Ile His Glu Lys Gly Phe Tyr Tyr Ile Tyr Ser Gln Thr Tyr Phe
    50                  55                  60

Arg Phe Gln Glu Glu Ile Lys Glu Asn Thr Lys Asn Asp Lys Gln Met
65                  70                  75                  80

Val Gln Tyr Ile Tyr Lys Tyr Thr Ser Tyr Pro Asp Pro Ile Leu Leu
                85                  90                  95

Met Lys Ser Ala Arg Asn Ser Cys Trp Ser Lys Asp Ala Glu Tyr Gly
            100                 105                 110

Leu Tyr Ser Ile Tyr Gln Gly Gly Ile Phe Glu Leu Lys Glu Asn Asp
        115                 120                 125

Arg Ile Phe Val Ser Val Thr Asn Glu His Leu Ile Asp Met Asp His
    130                 135                 140

Glu Ala Ser Phe Phe Gly Ala Phe Leu Val Gly Gly Gly Gly Gly
145                 150                 155                 160

Val Arg Glu Arg Gly Pro Gln Arg Val Ala Ala His Ile Thr Gly Thr
                165                 170                 175

Arg Gly Arg Ser Asn Thr
        180

<210> SEQ ID NO 17
<211> LENGTH: 35
<212> TYPE: DNA
<213> ORGANISM: artificial sequence
<220> FEATURE:
<223> OTHER INFORMATION: primer for the wild-type human TRAIL encoding
      gene

<400> SEQUENCE: 17
cgttcatatg gtgagagaaa gaggtcctca gagag                              35

<210> SEQ ID NO 18
<211> LENGTH: 39
<212> TYPE: DNA
<213> ORGANISM: artificial sequence
<220> FEATURE:
<223> OTHER INFORMATION: primer for the wild-type human TRAIL encoding
      gene

<400> SEQUENCE: 18
cttaggatcc ttagccaact aaaaaggccc cgaaaaaac                          39

-continued

```
<210> SEQ ID NO 19
<211> LENGTH: 30
<212> TYPE: DNA
<213> ORGANISM: artificial sequence
<220> FEATURE:
<223> OTHER INFORMATION: primer for a recombinant human circularly
      permuted TRAIL

<400> SEQUENCE: 19
catgcatatg acattgtctt ctccaaactc                               30

<210> SEQ ID NO 20
<211> LENGTH: 61
<212> TYPE: DNA
<213> ORGANISM: artificial sequence
<220> FEATURE:
<223> OTHER INFORMATION: primer for a recombinant human circularly
      permuted TRAIL

<400> SEQUENCE: 20
agttatgtga gctgctacac caccaccacc accgccaact aaaaaggccc caaaaaact    60 g                                                                  61

<210> SEQ ID NO 21
<211> LENGTH: 59
<212> TYPE: DNA
<213> ORGANISM: artificial sequence
<220> FEATURE:
<223> OTHER INFORMATION: primer for a recombinant human circularly
      permuted TRAIL

<400> SEQUENCE: 21
cgggatcctt atgtgttgct tcttcctctg gtcccagtta tgtgagctgc tacaccacc    59

<210> SEQ ID NO 22
<211> LENGTH: 37
<212> TYPE: DNA
<213> ORGANISM: artificial sequence
<220> FEATURE:
<223> OTHER INFORMATION: primer for NCPT-1

<400> SEQUENCE: 22
ggaattccat atgacattgt cttctccaaa ctccaag                            37

<210> SEQ ID NO 23
<211> LENGTH: 41
<212> TYPE: DNA
<213> ORGANISM: artificial sequence
<220> FEATURE:
<223> OTHER INFORMATION: primer for NCPT-1

<400> SEQUENCE: 23
cgggatccgc caactaaaaa ggccccaaaa aaactggctt c                       41

<210> SEQ ID NO 24
<211> LENGTH: 64
<212> TYPE: DNA
<213> ORGANISM: artificial sequence
<220> FEATURE:
<223> OTHER INFORMATION: primer for NCPT-1

<400> SEQUENCE: 24
agttatgtga gctgctactc taccaccacc accaccgcca actaaaaagg cccaaaaaa    60 actg                                                               64
```

```
<210> SEQ ID NO 25
<211> LENGTH: 62
<212> TYPE: DNA
<213> ORGANISM: artificial sequence
<220> FEATURE:
<223> OTHER INFORMATION: primer for NCPT-1

<400> SEQUENCE: 25
cgggatcctt atgtgttgct tcttcctctg gtcccagtta tgtgagctgc tactctacca      60
cc                                                                    62

<210> SEQ ID NO 26
<211> LENGTH: 64
<212> TYPE: DNA
<213> ORGANISM: artificial sequence
<220> FEATURE:
<223> OTHER INFORMATION: primer for NCPT-2

<400> SEQUENCE: 26
agaaatggtt tcctcagagg taccaccacc accaccgcca actaaaaagg ccccaaaaaa      60
actg                                                                  64

<210> SEQ ID NO 27
<211> LENGTH: 61
<212> TYPE: DNA
<213> ORGANISM: artificial sequence
<220> FEATURE:
<223> OTHER INFORMATION: primer for NCPT-2

<400> SEQUENCE: 27
tctcactagg ggagaaatat tttgttgctt tcttgaact gtagaaatgg tttcctcaga       60
g                                                                     61

<210> SEQ ID NO 28
<211> LENGTH: 61
<212> TYPE: DNA
<213> ORGANISM: artificial sequence
<220> FEATURE:
<223> OTHER INFORMATION: primer for NCPT-2

<400> SEQUENCE: 28
cagttatgtg agctgctact ctctgaggac ctctttctct cactagggga gaaatatttt     60
g                                                                     61

<210> SEQ ID NO 29
<211> LENGTH: 53
<212> TYPE: DNA
<213> ORGANISM: artificial sequence
<220> FEATURE:
<223> OTHER INFORMATION: primer for NCPT-2

<400> SEQUENCE: 29
cgggatcctt atgtgttgct tcttcctctg gtcccagtta tgtgagctgc tac            53

<210> SEQ ID NO 30
<211> LENGTH: 77
<212> TYPE: DNA
<213> ORGANISM: artificial sequence
<220> FEATURE:
<223> OTHER INFORMATION: primer for NCPT-3

<400> SEQUENCE: 30
gagctgctac tctctgagga cctctttctc tcacaccacc accaccaccg ccaactaaaa     60
```

```
aggccccaaa aaaactg                                                  77
```

```
<210> SEQ ID NO 31
<211> LENGTH: 62
<212> TYPE: DNA
<213> ORGANISM: artificial sequence
<220> FEATURE:
<223> OTHER INFORMATION: primer for NCPT-3

<400> SEQUENCE: 31
cgggatcctt atgtgttgct tcttcctctg gtcccagtta tgtgagctgc tactctctga    60
gg                                                                  62
```

```
<210> SEQ ID NO 32
<211> LENGTH: 50
<212> TYPE: DNA
<213> ORGANISM: artificial sequence
<220> FEATURE:
<223> OTHER INFORMATION: primer for NCPT-1.M1

<400> SEQUENCE: 32
catgccatgg gccaccacca ccaccaccac acattgtctt ctccaaactc               50
```

```
<210> SEQ ID NO 33
<211> LENGTH: 62
<212> TYPE: DNA
<213> ORGANISM: artificial sequence
<220> FEATURE:
<223> OTHER INFORMATION: primer for NCPT-1.M2

<400> SEQUENCE: 33
cgggatcctt agtggtggtg gtggtggtgt gtgttgcttc ttcctctggt cccagttatg    60
tg                                                                  62
```

```
<210> SEQ ID NO 34
<211> LENGTH: 32
<212> TYPE: DNA
<213> ORGANISM: artificial sequence
<220> FEATURE:
<223> OTHER INFORMATION: primer for NCPT-1.M2

<400> SEQUENCE: 34
catgccatgg gcacattgtc ttctccaaac tc                                 32
```

```
<210> SEQ ID NO 35
<211> LENGTH: 41
<212> TYPE: DNA
<213> ORGANISM: artificial sequence
<220> FEATURE:
<223> OTHER INFORMATION: primer for NCPT-1.M3

<400> SEQUENCE: 35
catgccatgg gccaccacca cacattgtct tctccaaact c                       41
```

```
<210> SEQ ID NO 36
<211> LENGTH: 48
<212> TYPE: DNA
<213> ORGANISM: artificial sequence
<220> FEATURE:
<223> OTHER INFORMATION: primer for NCPT-1.M4

<400> SEQUENCE: 36
catgcatatg caccaccacc accaccacac attgtcttct ccaaactc                48
```

<210> SEQ ID NO 37
<211> LENGTH: 147
<212> TYPE: PRT
<213> ORGANISM: artificial sequence
<220> FEATURE:
<223> OTHER INFORMATION: amino acids 135-281 of TRAIL

<400> SEQUENCE: 37

Thr Leu Ser Ser Pro Asn Ser Lys Asn Glu Lys Ala Leu Gly Arg Lys
1               5                   10                  15

Ile Asn Ser Trp Glu Ser Ser Arg Ser Gly His Ser Phe Leu Ser Asn
            20                  25                  30

Leu His Leu Arg Asn Gly Glu Leu Val Ile His Glu Lys Gly Phe Tyr
        35                  40                  45

Tyr Ile Tyr Ser Gln Thr Tyr Phe Arg Phe Gln Glu Glu Ile Lys Glu
    50                  55                  60

Asn Thr Lys Asn Asp Lys Gln Met Val Gln Tyr Ile Tyr Lys Tyr Thr
65              70                  75                  80

Ser Tyr Pro Asp Pro Ile Leu Leu Met Lys Ser Ala Arg Asn Ser Cys
            85                  90                  95

Trp Ser Lys Asp Ala Glu Tyr Gly Leu Tyr Ser Ile Tyr Gln Gly Gly
        100                 105                 110

Ile Phe Glu Leu Lys Glu Asn Asp Arg Ile Phe Val Ser Val Thr Asn
    115                 120                 125

Glu His Leu Ile Asp Met Asp His Glu Ala Ser Phe Phe Gly Ala Phe
130                 135                 140

Leu Val Gly
145

<210> SEQ ID NO 38
<211> LENGTH: 15
<212> TYPE: PRT
<213> ORGANISM: artificial sequence
<220> FEATURE:
<223> OTHER INFORMATION: amino acids 121-135 of TRAIL

<400> SEQUENCE: 38

Arg Val Ala Ala His Ile Thr Gly Thr Arg Gly Arg Ser Asn Thr
1               5                   10                  15

<210> SEQ ID NO 39
<211> LENGTH: 41
<212> TYPE: PRT
<213> ORGANISM: artificial sequence
<220> FEATURE:
<223> OTHER INFORMATION: amino acids 95-135 of TRAIL

<400> SEQUENCE: 39

Thr Ser Glu Glu Thr Ile Ser Thr Val Gln Glu Lys Gln Gln Asn Ile
1               5                   10                  15

Ser Pro Leu Val Arg Glu Arg Gly Pro Gln Arg Val Ala Ala His Ile
            20                  25                  30

Thr Gly Thr Arg Gly Arg Ser Asn Thr
        35                  40

<210> SEQ ID NO 40
<211> LENGTH: 22
<212> TYPE: PRT
<213> ORGANISM: artificial sequence
<220> FEATURE:
<223> OTHER INFORMATION: amino acids 114-135 of TRAIL

```
<400> SEQUENCE: 40

Val Arg Glu Arg Gly Pro Gln Arg Val Ala Ala His Ile Thr Gly Thr
1               5                   10                  15

Arg Gly Arg Ser Asn Thr
            20

<210> SEQ ID NO 41
<211> LENGTH: 5
<212> TYPE: PRT
<213> ORGANISM: artificial sequence
<220> FEATURE:
<223> OTHER INFORMATION: linker

<400> SEQUENCE: 41

Gly Gly Gly Gly Gly
1               5

<210> SEQ ID NO 42
<211> LENGTH: 5
<212> TYPE: PRT
<213> ORGANISM: artificial sequence
<220> FEATURE:
<223> OTHER INFORMATION: linker

<400> SEQUENCE: 42

Gly Ser Gly Gly Gly
1               5

<210> SEQ ID NO 43
<211> LENGTH: 7
<212> TYPE: PRT
<213> ORGANISM: artificial sequence
<220> FEATURE:
<223> OTHER INFORMATION: linker

<400> SEQUENCE: 43

Gly Gly Ser Gly Gly Gly Gly
1               5

<210> SEQ ID NO 44
<211> LENGTH: 8
<212> TYPE: PRT
<213> ORGANISM: artificial sequence
<220> FEATURE:
<223> OTHER INFORMATION: synthetic

<400> SEQUENCE: 44

Met Gly His His His His His His
1               5

<210> SEQ ID NO 45
<211> LENGTH: 6
<212> TYPE: PRT
<213> ORGANISM: artificial sequence
<220> FEATURE:
<223> OTHER INFORMATION: synthetic

<400> SEQUENCE: 45

His His His His His His
1               5

<210> SEQ ID NO 46
<211> LENGTH: 5
<212> TYPE: PRT
<213> ORGANISM: artificial sequence
<220> FEATURE:
```

```
<223> OTHER INFORMATION: synthetic

<400> SEQUENCE: 46

Met Gly His His His
1               5

<210> SEQ ID NO 47
<211> LENGTH: 11
<212> TYPE: PRT
<213> ORGANISM: artificial sequence
<220> FEATURE:
<223> OTHER INFORMATION: synthetic

<400> SEQUENCE: 47

Met Gly His His His His His His His His
1               5                   10

<210> SEQ ID NO 48
<211> LENGTH: 8
<212> TYPE: PRT
<213> ORGANISM: artificial sequence
<220> FEATURE:
<223> OTHER INFORMATION: synthetic

<400> SEQUENCE: 48

Met Gly Asn Asn Asn Asn Asn Asn
1               5
```

FUSION PROTEIN COMPRISING CIRCULARLY PERMUTED FORM OF TRAIL/APO2L, CODING GENE AND USE THEREOF

CROSS-REFERENCE To RELATED APPLICATIONS

This application is a U.S. national phase application filed under 35 U.S.C. §371 of International Application PCT/CN2011/001573, filed Sep. 16, 2011, designating the United States, which is hereby incorporated herein by reference in its entirety.

REFERENCE To A SEQUENCE LISTING

The Sequence Listing associated with this application is filed in electronic format via EFS-Web and is hereby incorporated into the specification in its entirety. The name of the text file containing the Sequence Listing is "FPCH1116013P_110916_SEQUENCE_LISTING." The size of the text file is 30.9 KB, and the text file was created on Mar. 7, 2014.

BACKGROUND ART

The concept of apoptosis was first proposed in 1972 by Kerr et al, and refers to a well organized and autonomous death form different from cell necrosis, which is controlled by multiple genes. It plays an indispensable role in the evolution, homeostatic process and development of multiple systems of organisms (Renehan et al., 2001; Nijhawan et al., 2000; Opferman and Korsmeyer, 2003; Osborne, 1996). The mechanism of apoptosis is highly complicated, and involves the implication of a series of energy-dependent cascade reactions. Till now, two major apoptotic pathways have been found: extrinsic pathway or death receptor pathway and intrinsic pathway or mitochondrial pathway, and there is a link between the two pathways (Igney and Krammer, 2002); there is another pathway known as perforin/granzyme pathway, whereby granzyme A or granzyme B is involved in T cell-mediated cytotoxicity and perforin-granzyme dependent cell killing. Finally, the extrinsic pathway, intrinsic pathway and granzyme B pathway converge to the same execution pathway, i.e. caspase-3 cleavage, DNA breakage, cytoskeletal and nucleoprotein degradation, protein crosslink, formation of apoptotic bodies, expression of ligand of phagocytic cell receptor, and eventually being swallowed. The apoptosis triggered by extrinsic pathway requires the interaction between ligands and transmembrane death receptors, and these death receptors belong to the tumor necrosis factor (TNF) receptor superfamily (Locksley et al., 2001). The members of TNF receptor superfamily share similar cysteine-rich extracellular binding domain and an intracellular death domain with approximately 80 amino acids (Ashkenazi and Dixit, 1998). Death domain plays a key role in the transmission of death signals from the cell surface to inside of the cell, at present, the well-established ligand/death receptor pathways include FasL/FasR, TNF-α/TNFR1, Apo3L/DR3, Apo2L/DR4 and Apo2L/DR5 (Chicheportiche et al., 1997; Ashkenazi et al., 1998; Peter and Kramer, 1998; Suliman et al., 2001; Rubio-Moscardo et al., 2005).

Apoptosis occurs under many physiological conditions, such as embryonic development, and clonal selection in the immune system (Itoh et al., 1991). Apoptosis under the physiological conditions is controlled by precise regulation, and excessively upregulation or downregulation of apoptosis will result in pathological changes, such as developmental defects, autoimmune disease, neurodegenerative disease, or malignancy and the like. Malignancy is now considered as the result of excessive cell proliferation and/or decrease of cell removal due to the dysfunction of the normal cell cycle control mechanisms (King and Cidlowski, 1998). The inhibition of apoptosis plays a key role in the onset and development of some tumors (Kerr et al., 1994).

In tumor cells, its apoptosis can be inhibited through a variety of molecular mechanisms, such as the expression of anti-apoptotic protein, downregulation of expression of pro-apoptotic proteins or inactivation of mutation of pro-apoptotic protein. Based on the understanding of the role of apoptosis in the onset and development of tumor and signal transduction pathways of apoptosis, drugs promoting apoptosis of tumor cells have been developed or are developed. The development of the novel drugs targeting extracellular apoptotic pathway of the death receptor is one research focus of recent years, in particular, DR4/DR5. Several drug candidates targeting DR4/DR5 are now in clinical trials.

TNF related apoptosis inducing ligand (TRAIL) gene was first cloned and named by Wiley, et al. in 1995. In 1996, the same gene was cloned and named as Apo2L by Pitti et al. TRAIL/Apo2L is widely expressed in various tissues of normal human (lung, liver, kidney, spleen, thymus, prostate, ovary, small intestine, peripheral lymphocytes, heart, placenta, skeletal muscle, etc.) (Wiley et al., 1995; Pitti et al., 1996). TRAIL/Apo2L exists in vivo in two forms, i.e., membrane-bound and soluble TRAIL/Apo2L, both of which can form a stable homotrimer and bind with receptor to perform biological effects. A large number of in vivo and in vitro experiments show that, TRAIL/Apo2L can selectively induce apoptosis of several tumor cells and transformed cells; application of recombinant TRAIL/Apo2L protein in tumor-bearing animals can significantly inhibit tumor cell growth and even result in tumor regression without obvious damage to the host. The specificity, efficiency and non-toxicity of TRAIL/Apo2L killing tumor cells are significantly advantageous than that of CD95L and TNFα in the same family, since the latter can lead to the systemic and hard-to-be-controlled inflammation and severe toxicity such as degeneration, necrosis, hemorrhage to liver tissue, and even death (Tartaglia L, 1992). The anti-tumor activity and safety of TRAIL/Apo2L are significantly advantageous than the clinically used radiotherapy and chemotherapy etc. Animal experiments have confirmed that, TRAIL/Apo2L combined with radiotherapy and chemotherapy can produce a synergistic effect, thereby reducing the dosage and side effects of the latter. Therefore, TRAIL/Apo2L is now considered as the most promising anticancer drugs. Immunex Inc. (U.S.) discloses the gene sequence, expression vectors, and host cells of the wild-type TRAIL, and anti-TRAIL antibody (US6284236). Genentech, Inc. (U.S.) discloses a method of using wild-type APO2L for treatment of breast, colon, lung, prostate and glioma cancer (US6030945, US6746668, US6998116). The other two patent applications to Genentech Inc. disclose certain amino acid positions in APO2L polypeptide were replaced (US6740739; WO 03/029420A2). Due to low activity of the recombinantly prepared soluble wild type TRAIL/APO2L, it is not applicable for industrial and clinical applications, therefore, the structure of wild-type TRAIL/APO2L is reconstructed and modified to acquire a permuted TRAIL/APO2L with high activity is a main way to develop these drugs.

WO2005/042744 discloses a circularly permuted form of TRAIL, which has a significant selective inhibitory effect on tumor.

SUMMARY OF THE INVENTION

The present invention relates to a fusion protein comprising circularly permuted form of TRAIL, which:

(1) is the fusion protein comprising circularly permuted form of TRAIL and oligopeptides located at the N-terminus and/or C-terminus of the permuted form, the oligopeptides contain a repeating sequence consisting of 3-10 histidine residues, and the components of the circularly permuted form of TRAIL from N-terminus to C-terminus are: (a) amino acids 135-281 of TRAIL, (b) a linker, and (c) amino acids 121-135 of TRAIL or amino acids 114-135 of TRAIL or amino acids 95-135 of TRAIL or any fragments of amino acids 95-135 of TRAIL containing amino acids 121-135 of TRAIL; or (2) is the fusion protein comprising circularly permuted form of TRAIL having at least 80%, preferably 85%, 90%, 95%, 96%, 97%, 98%, or 99% amino acid sequence identity to (1), the fusion protein comprising circularly permuted form of TRAIL has a tumor inhibitory activity which is at least 20%, e.g. 90-110%, 80-120%, 70-130%, 60-140%, 50-150%, 40-160%, 30-170%, 20-180%, or above of that of the fusion protein comprising circularly permuted form of TRAIL as set forth in SEQ ID NO: 5. The identity is calculated using procedures well known in the art, for example, BLAST, using default parameters, see, e.g., Altschul et al., J. Mol. Biol. 1990; 215: 403-410; Altschul et al., Nucleic Acids Res. 1997; 25: 3389-402 (1997). In some embodiments, the difference thereof from (1) exists only in the amino acid sequence of the circularly permuted form of TRAIL. In further embodiments, the difference thereof from (1) exists only in the amino acid sequence of (a), (b) and/or (c) of the circularly permuted form of TRAIL. In some embodiments, the difference thereof from (1) exists only in the amino acid sequence other than the circularly permuted form of TRAIL. In some embodiments, the difference thereof from (1) exists in the amino acid sequence in the circularly permuted form of TRAIL as well as that other than the circularly permuted form of TRAIL.

(3) is the fusion protein comprising circularly permuted form of TRAIL derived from amino acid sequence of (1) by substitution, deletion or addition of one or more amino acids residues, the fusion protein comprising circularly permuted form of TRAIL has a tumor inhibitory activity which is at least 20%, e.g. 90-110%, 80-120%, 70-130%, 60-140%, 50-150%, 40-160%, 30-170%, 20-180%, or above of that of the fusion protein comprising circularly permuted form of TRAIL as set forth in SEQ ID NO: 5. In some embodiments, the difference thereof from (1) exists only in the amino acid sequence of the circularly permuted form of TRAIL. In further embodiments, the difference thereof from (1) exists only in the amino acid sequence of (a), (b) and/or (c) of the circularly permuted form of TRAIL. In some embodiments, the difference thereof from (1) exists only in the amino acid sequence other than the circularly permuted form of TRAIL. In some embodiments, the difference thereof from (1) exists in the amino acid sequence in the circularly permuted form of TRAIL as well as that other than the circularly permuted form of TRAIL. In some embodiments, the number of amino acid residues subjected to substitution, deletion or addition is 1-20, 1-15, 1-14, 1-13, 1-12, 1-11, 1-10, 1-9, 1-8, 1-7, 1-6, 1-5, 1-4, 1-3, 1-2, or 1.

Said "tumor inhibitory activity" can be characterized by its inhibitory activity on tumor cell lines, e.g., lung cancer, multiple myeloma and/or colon tumor cell lines etc. In some embodiments, the tumor inhibitory activity can be characterized by IC50 of the killing activity on tumor cell lines. In some embodiments, the "tumor inhibitory activity" can be characterized by its inhibitory activity on lung cancer cell lines. In some embodiments, the tumor inhibitory activity can be characterized by IC50 of the killing activity on lung cancer cell line, e.g. can be characterized by IC50 measured by the method as described herein in Example 6.

Said "any fragments of amino acids 95-135 of TRAIL containing amino acids 121-135 of TRAIL" refers to an amino acid fragment of TRAIL, whose N-terminus is at any position between the positions 95-121 of TRAIL and C-terminus is at position 135 of TRAIL.

In some embodiments, the number of histidine residues in the oligopeptide at the N-terminus and/or C-terminus in the fusion protein of the present invention is 3-9, preferably 6-9.

In some embodiments, the oligopeptide at the N-terminus in the fusion protein of the present invention comprise structure $MG_a$-$His_b$, wherein a is 0 or 1, and b is an integer between 3 to 9, preferably an integer between 6 to 9.

The linker as described herein is the linker generally used in the fusion protein art, and one skilled in the art can readily design and prepare such a linker. In some embodiments, the linker in the fusion protein of the present invention is 3-15 amino acids in length, preferably 3-10 amino acids, more preferably 5-7 amino acids, preferably, the amino acid sequence of the linker is consisting of several Gs or consisting of several continuous Gs interspersed with one S, and more preferably, the amino acid sequence of the linker is selected from the group consisting of SEQ ID NO:41, 42 and 43.

The TRAIL as described herein include various TRAILs, including natural TRAIL and unnatural TRAIL, preferably wild-type human TRAIL disclosed in the prior art (Wiley et al., 1995; Pitti et al., 1996). In some embodiments, in the fusion protein of the present invention, the sequence of the amino acids 135-281 of TRAIL is SEQ ID NO:37, the sequence of the amino acids 121-135 of TRAIL is SEQ ID NO:38, the sequence of the amino acids 95-135 of TRAIL is SEQ ID NO:39, and the sequence of the amino acids 114-135 of TRAIL is SEQ ID NO:40.

The amino acid positions of TRAIL as described herein are the positions in the above wild-type TRAIL, or the corresponding positions when optimally aligned with the above wild-type TRAIL. The alignment is carried out using procedures well known in the art, for example, BLAST, using default parameters, see, e.g., Altschul et al., J. Mol. Biol. 1990; 215: 403-410; Altschul et al., Nucleic Acids Res. 1997; 25: 3389-402 (1997).

In some embodiments, the sequence of the fusion protein of the present invention is selected from the group consisting of SEQ ID NO: 5-11 and 15-16.

The present invention also relates to an isolated nucleic acid encoding the fusion protein of the invention. The present invention also relates to a vector, preferably an expression vector, comprising the nucleic acid encoding the fusion protein of the invention. The present invention also relates to a host cell comprising the above vector, and the host cell is from bacteria, fungi, plants, animals, humans, etc., e.g., *Escherichia coli*.

The present invention also relates to a pharmaceutical composition for treatment of tumor comprising the fusion protein of the present invention, optionally further comprising one or more additional drug(s) for treatment of tumor.

The present invention also relates to a kit for treatment of tumor comprising the fusion protein of the present invention, and optionally one or more additional drug(s) for treatment of tumor. In the kit, the fusion protein and additional drug(s) for treatment of tumor are mixed together or placed separately.

The present invention also relates to a method for treatment of tumor comprising administering to a subject the fusion protein of the invention, optionally further comprising administering to the subject one or more additional drug(s) for treatment of tumor, wherein the fusion protein can be administered simultaneously or sequentially with the additional drug(s).

The present invention also relates to use of the fusion protein of the invention or the composition comprising the fusion protein in the manufacture of a medicament for treatment of tumor, wherein said medicament optionally further comprises one or more additional drug(s) for treatment of tumor.

In some embodiments of the present invention, terms "comprise/comprising", "include/including", "have/having" as used herein all encompass "consisting of . . . ".

The tumors as described herein include, but are not limited to, multiple myeloma, lymphoma, splenic tumor, melanoma, neuroglioma, mediastinal tumor, ureter tumor, gynecological tumor, endocrine system tumor, central nervous system tumor, lung cancer, colon cancer, gastric cancer, esophageal cancer, intestinal cancer, liver cancer, pancreatic cancer, rectal cancer, kidney adenocarcinoma, bladder cancer, prostate cancer, urethral cancer, testicular cancer, ovarian cancer, breast cancer, leukemia and the like. In some embodiments, the tumor(s) is(are) selected from lung cancer, multiple myeloma, and colon cancer.

The additional drug(s) for treatment of tumor as described herein include(s), but are not limited to, melphalan, dexamethasone, thalidomide, lenalidomide, Velcade, vincristine, vinorelbine, doxorubicin, liposomal doxorubicin, cyclophosphamide, irinotecan, prednisone, paclitaxel, carboplatin, cisplatin, VP16, 5-FU and the like. In some embodiments, the additional drug(s) for treatment of tumor is(are) selected from the group consisting of melphalan, prednisone, paclitaxel, and carboplatin.

BRIEF DESCRIPTION OF THE FIGURES

FIG. 1. Observation of the killing effect of NCPT-1.M1 on H460 cells under phase contrast microscope.

FIG. 2. The time-effect relationship of NCPT-1.M1 in killing RPMI8226 cells. Incubation of varying concentration of NCPT-1.M1 with human multiple myeloma RPMI8226 cells for 6 h could result in maximum killing, without significant difference from those for 8 h, 24 h, and 48 h.

FIG. 3. The morphological change of the apoptosis of human multiple myeloma cell RPMI 8226 induced by NCPT-1.M1. The cells were incubated with NCPT-1.M1 (200 ng/ml) for 3 h and then prepared as smears before MGG staining. A(1000×), C(200×) represent the control group, wherein the cytoplasms are basophilic and stained as blue, the nucleus are eosinophilic, stained as homogeneous red with clear nucleoli; B(1000×), D(200×) represent NCPT-1.M1 group, the membranes are intact but with large bubbles, the chromatin exhibits aggregation at the periphery, karyopyknosis, and karyorrhexis with darker staining.

FIG. 4. TUNEL assay of apoptosis of human lung cancer cell line NCI-H460 induced by NCPT-1.M1. The NCI-H460 cells were incubated with NCPT-1.M1 (15 ng/ml) for 4 h and then prepared as smears before TUNEL staining. Almost all of the tumor cells exhibit characteristic of apoptosis as karyopyknosis, karyorrhexis, and brown staining of the fractured chromatins etc under microscope (B). In control group, nucleus remains intact, and no characteristic brown stained chromatins are seen (A).

FIG. 5. The agarose gel electrophoresis analysis of internucleosomal DNA fragmentation of NCI-H460 cells after incubated with NCPT-1.M1 for varying time.

Marker: 200 bp-2000 bp DNA markers with 200 bp interval;

Control: solvent control;

2 h, 4 h, 6 h: represent incubation with 15 ng/ml NCPT-1.M1 for 2 h, 4 h, 6 h, respectively.

FIG. 6. Caspase-8 inhibitor (zIETD-fmk) can inhibit the pro-apoptotic activity of NCPT-1.M1 on H460 cells.

H460 cells were incubated with NCPT-1.M1 (1.2 or 10 ng/ml) in the presence or absence of Caspase-8 inhibitor zIETD-fmk (concentration of 30 μmmol/L, added 1 h earlier than NCPT-1.M1) for 24 h, and then cell survival rate was measured by MTT assay.

FIG. 7. NCPT-1.M1 can result in apoptosis of a large number of tumor cells in tumor tissue.

Athymic nude mice were subcutaneously inoculated with human MM RPMI8226 tumor cells and treated with NCPT-1.M1, then tumor tissue was resected and subjected to conventional HE staining (A, B) and TUNEL staining of apoptotic cells (C, D). A large number of cells exhibit karyopycnosis, karyorrhexis (B), brown staining of nuclei (D) and other characteristics of apoptosis, while there are only a few apoptotic cells in the control group (A, C).

FIG. 8. The growth of human PRMI 8226 xenograft tumor in mice is significantly inhibited by NCPT-1.M1. Athymic nude mice (Beijing Huafukang Biotechnology Co., Ltd.) were subcutaneously inoculated with RPMI8226 tumor cells ($5 \times 10^6$/mouse). When the tumor grew to about 500 mm³, the mice were divided into several groups, which were intraperitoneally injected with normal saline (control group), NCPT-1.M1 (15 mg/kg) and wild-type TRAIL (wtTRAIL, 15 mg/kg or 45 mg/kg) respectively once a day for 8 consecutive days. The tumor volumes were measured with a vernier caliper every two days. Tumor growth rate of NCPT-1.M1 group with a dose of 15 mg/kg is significantly lower than that of wtTRAIL group with a dose of 45 mg/kg, suggesting that NCPT-1.M1 has an inhibitory activity stronger than that of wtTRAIL on RPMI8226 xenograft tumor.

FIG. 9. NCPT-1.M1 combined with melphalan can improve the killing effect on human multiple myeloma cell line U266. U266 cells are insensitive to CPT. At the concentration of 1 μg/ml, NCPT-1.M1 alone has a mild killing effect on U266 (<20%), but with the presence of melphalan (12.5~50 μg/ml), both of them can cause enhanced killing effect. The cell viability was assayed with ATPlite luminescent system (PerkinElmer), the data as shown in this figure are all represented as the mean±standard deviation, n=4, #P<0.05, ##P<0.01 vs. melphalan group; *P<0.05 vs. NCPT-1.M1 group.

FIG. 10. NCPT-1.M1 combined with melphalan has a synergistic killing effect on human MM cell line H929. The melphalan (12.5 μg/ml) combined with varying concentrations of NCPT-1.M1 (31~1000 ng/ml) were incubated with H929 cells. The cell survival rate was assayed with ATPlite luminescent system (PerkinElmer). A combination index (CI, marked above the histogram) represents the nature of the interaction between the two drugs: CI<0.9 represents a synergistic effect, CI>1.1 represents an antagonistic effect, and CI between 0.9 and 1.1 represents an additive effect.

FIG. 11. NCPT-1.M1 combined with melphalan has a synergistic killing effect on human MM cell line RPMI8226. The melphalan (25 μg/ml) combined with varying concentrations of NCPT-1.M1 (2~500 ng/ml) were incubated with RPMI8226 cells. The cell survival rate was assayed with ATPlite luminescent system (PerkinElmer). A combination index (CI, marked above the histogram) represents the nature of the interaction between the two drugs: CI<0.9 represents a synergistic effect, CI>1.1 represents an antagonistic effect, and CI between 0.9 and 1.1 represents an additive effect.

FIG. 12. The inhibitory effect of NCPT-1.M1 on the growth of human PRMI 8226 xenograft tumor in mice is significantly enhanced by NCPT-1.M1 combined with Melphalan and Prednisone.

FIG. 13. The inhibitory effect of NCPT-1.M1 on the growth of human PRMI 8226 xenograft tumor in mice is significantly enhanced by NCPT-1.M1 combined with chemotherapy (PC regimen: paclitaxel plus carboplatin).

DESCRIPTION OF THE PREFERRED EMBODIMENTS

EXAMPLE 1

Construction of the Wild-Type Human TRAIL Encoding Gene

A plasmid containing a gene expressing the sequence of amino acid 114-281 of wild-type human TRAIL was constructed.

(1) The First Step PCR

PCR was carried out with human spleen cDNA library (Clontech) as a template and P1, P2 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

```
                                                    (SEQ ID NO: 17)
P1: cgttcatatg gtgagagaaagaggtcctcagagag (SEQ ID NO: 18)
P2: ctta ggatcc ttagccaactaaaaaggccccgaaaaaac
```

(2) Construction of TRAIL Plasmid

The resulting PCR product of the preceding step was purified, digested with restriction endonucleases Nde I and BamH I, ligated with T4 ligase into the digested vector pET42a with the same endonucleases, cultured on plate and propogated before plasmid isolation, digestion test and preliminary screen of positive clones. The expression plasmid of recombinant human TRAIL gene was confirmed by DNA sequencing, and the contructed plasmid is named as pET42a-TRAIL114-281.

EXAMPLE 2

Construction of a Gene Expressing a Recombinant Human Circularly Permuted TRAIL A gene encoding a recombinant human circularly permuted TRAIL (Circularly Permuted TRAIL, referred to as CPT) was constructed. The amino acid sequences encoded by said gene from N-terminus to C-terminus are: (a) amino acids 135-281 of TRAIL, (b) a linker, and (c) amino acids 122-135 of TRAIL.

```
CPT polypeptide sequence
                                               (SEQ ID NO: 1)
(TLSSPNSKNEKALGRKINSWESSRSGHSFLSNLHLRNGELVIHEK

GFYYIYSQTYFRFQEEI

KENTKNDKQMVQYIYKYTSYPDPILLMKSARNSCWSKDAEYGLY

SIYQGGIFELKENDRI FVSVTNEHLI

DMDHEASFFGAFLVGGGGGGVAAHITGTR GRSNT)
```

(1) The First Step PCR Amplification

PCR was carried out with plasmid pET42a-TRAIL114-281 as a template and P3, P4 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

```
                                                    (SEQ ID NO: 19)
P3: catgcatatgacattg tcttctccaa actc (SEQ ID NO: 20)
P4: agttatgtgagctgctacaccaccaccaccaccgccaactaaaaaggccccaaaaaaactg
```

(2) The Second Step PCR

PCR was carried out with the PCR product from the first step as a template and P3, P5 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

```
                                                    (SEQ ID NO: 21)
P5: cgggatccttatgtgttgcttcttcctctggtcccagttatgtgagctgctacaccacc (BamHI restriction site)
```

(3) Construction of CPT Plasmid

The PCR product from the second step was purified, digested with restriction endonucleases Nde I and BamH I, ligated with T4 ligase into the digested vector pET42a with the same endonucleases, cultured on plate and propogated before plasmid isolation, digestion test and preliminary screen of positive clones. The expression plasmid of the recombinant human circularly permuted TRAIL was confirmed by DNA sequencing, and the contructed plasmid is named as pET42a-CPT.

EXAMPLE 3

Construction of Novel Genes Encoding Various Recombinant Human Circularly Permuted TRAILs 1. Construction of a gene encoding recombinant human New Circularly Permuted TRAIL-1 (New Circularly Permuted TRAIL-1, referred to as NCPT-1).

The amino acid sequences encoded by said gene from N-terminus to C-terminus are: (a) amino acids 135-281 of TRAIL, (b) a linker, and (c) amino acids 121-135 of TRAIL.

```
NCPT-1 polypeptide sequence
                                     (SEQ ID NO: 2)
(TLSSPNSKNEKALGRKINSWESSRSGHSFLSNLHLRNGELVIHEK

GFYYIYSQTYFRFQEEI

KENTKNDKQMVQYIYKYTSYPDPILLMKSARNSCWSKDAEYGLY

SIYQGGIFELKENDRI FVSVTNEHLI

DMDHEASFFGAFLVGGGGGG RVAAHITGTR GRSNT)
```

(1) PCR Amplification of a Gene Encoding Amino Acids 135-281 of TRAIL

PCR was carried out with human spleen cDNA library (Clontech) as a template and P6, P7 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

```
                                     (SEQ ID NO: 22)
P6: ggaattccatatgacattgtcttctccaaactccaag(NdeI restriction site)
                                     (SEQ ID NO: 23)
P7: cgggatccgccaactaaaaaggccccaaaaaaactggcttc (BamH I restriction site)
```

The PCR product and plasmid pET42a (Novagen) were digested with the restriction endonucleases NdeI and BamH I, and ligated by T4 DNA ligase. The ligated product was transformed into the competent BL21 (DE3) (Invitrogen) bacteria. The transformed bacteria was cultured on plate and propogated before plasmid isolation, digestion test and preliminary screen of positive clones. The positive clones were then confirmed by DNA sequencing. The constructed plasmid is named as pET42a-TRAIL135-281.

(2) The Second Step PCR

PCR was carried out with plasmid pET42a-TRAIL135-281 as a template and P6, P8 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

```
                                                         (SEQ ID NO: 24)
P8: agttatgtgagctgctactctaccaccaccaccacgccaactaaaaaggccccaaaaaaactg
```

(3) The Third Step PCR

PCR was carried out with the PCR product from the second step as a template and P6, P9 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

```
                                                         (SEQ ID NO: 25)
P9: cgggatccttatgtgttgcttcttcctctggtcccagttatgtgagctgctactctaccacc(BamH I restriction site)
```

(4) Construction of NCPT-1 Plasmid

The PCR product from the third step was purified, digested with restriction endonucleases Nde I and BamH I, ligated with T4 ligase into the digested vector pET42a with the same endonucleases, cultured on plate and propogated before plasmid isolation, digestion test and preliminary screen of positive clones. The expression plasmid of recombinant human NCPT-1 gene was confirmed by DNA sequencing, and the contructed plasmid is named as pET42a-NCPT-1.

2. Construction of a gene encoding a recombinant human New Circularly Permuted TRAIL-2 (New Circularly Permuted TRAIL-2, referred to as NCPT-2).

The amino acid sequences encoded by said gene from N-terminus to C-terminus are: (a) amino acids 135-281 of TRAIL, (b) a linker, and (c) amino acids 95-135 of TRAIL.

NCPT-2 polypeptide sequence
(SEQ ID NO: 3)
(TLSSPNSKNEKALGRKINSWESSRSGHSFLSNLHLRNGELVIHEKG

FYYIYSQTYFRFQEEIKENTKNDKQMVQYIYKYTSYPDPILLMKSA

RNSCWSKDAEYGLYSIYQGG IFELKENDRI FVSVTNEHLI

DMDHEASFFGAFLVGGGGGG

TSEETISTVQEKQQNISPLVRERGPQ

RVAAHITGTR GRSNT)

(1) The First Step PCR

PCR was carried out with plasmid pET42a-TRAIL135-281 as a template and P6, P10 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

(SEQ ID NO: 26)
P10: agaaatggtttcctcagaggtaccaccaccaccaccgccaactaaaaaggccccaaaaaaactg (2) The Second Step PCR PCR was carried out with the PCR product from the first step as a template and P6, P11 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P11: (SEQ ID NO: 27)
tctcactaggggagaaatattttgttgcttttcttgaactgtaga aatggtttcctcagag (3) The Third Step PCR PCR was carried out with the PCR product from the second step as a template and P6, P12 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P12: (SEQ ID NO: 28)
cagttatgtgagctgctactctctgaggacctctttctctcacta ggggagaaatattttg (4) The Forth Step PCR PCR was carried out with the PCR product from the third step as a template and P6, P13 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P13: (SEQ ID NO: 29)
cg*ggatcc*ttatgtgttgcttcttcctctggtcccagttatgt gagctgctac (5) Construction of NCPT-2 Plasmid The PCR product from the forth step was purified, digested with restriction endonucleases Nde I and BamH I, ligated with T4 ligase into the digested vector pET42a with the same endonucleases, cultured on plate and propogated before plasmid isolation, digestion test and preliminary screen of positive clones. The expression plasmid of the recombinant human circularly permuted TRAIL (NCPT-2) was confirmed by DNA sequencing, and the contructed plasmid is named as pET42a-NCPT-2.

3. Construction of a gene encoding a recombinant human New Circularly Permuted TRAIL-3 (New Circularly Permuted TRAIL-3, referred to as NCPT-3).

The amino acid sequences encoded by said gene from N-terminus to C-terminus are: (a) amino acids 135-281 of TRAIL, (b) a linker, and (c) amino acids 114-135 of TRAIL.

NCPT-3 polypeptide sequence (SEQ ID NO: 4)
(TLSSPNSKNEKALGRKINSWESSRSGHSFLSNLHLRNGELVIHEKG

FYYIYSQTYFRFQEEIKENTKNDKQMVQYIYKYTSYPDPILLMKSA

RNSCWSKDAEYGLYSIYQGG IFELKENDRI

FVSVTNEHLIDMDHEASFFGAFLVGGGGGVRERGPQRVAAHITG

TR GRSNT)

(1) The First Step PCR

PCR was carried out with plasmid pET42a-TRAIL135-281 as a template and P6, P14 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P14: (SEQ ID NO: 30)
gagctgctactctctgaggacctctttctctcacaccaccaccac cgccaactaaaaaggcccaaaaaaactg (2) The Second Step PCR PCR was carried out with the PCR product from the first step as a template and P6, P15 as downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P15: (SEQ ID NO: 31)
cgggatccTta tgtgttgcttcttcctctggtcccagttatgtgagc tgctactctctgagg (3) Construction of NCPT-3 Plasmid The PCR product from the second step was purified, digested with restriction endonucleases Nde I and BamH I, ligated with T4 ligase into the digested vector pET42a with the same endonucleases, cultured on plate and propogated before plasmid isolation, digestion test and preliminary screen of positive clones. The expression plasmid of the recombinant human circularly permuted TRAIL (NCPT-3) was confirmed by DNA sequencing, and the contructed plasmid is named as pET42a-NCPT-3.

EXAMPLE 4

Construction of Genes Encoding Various Mutants of NCPT-1, NCPT-2, and NCPT-3

1. Construction of a Gene Encoding NCPT-1.M1

Met-Gly-His-His-His-His-His-His gene sequence was fused to the upstream of a gene encoding NCPT-1, i.e. Met-Gly-His-His-His-His-His-His amino acid sequence (SEQ ID NO: 44) was fused to the N-terminus of NCPT-1 polypeptide (MG+His6+NCPT-1).

NCPT-1.M1 polypeptide sequence (SEQ ID NO: 5)
MGHHHHHHTLSSPNSKNEKALGRKINSWESSRSGHSFLSNLHLRN

GELVIHEKGFYYIYSQTYFRFQEEIKENTKNDKQMVQYIYKYTSY

PDPILLMKSARNSCWSKDAEYGLYSIYQGGIFELKENDRIFVSVTN

EHLIDMDHEASFFGAFLVGGGGGRVAAHITGTRGRSNT

PCR was carried out with pET42a-NCPT-1 as a template and P16, P9 as a pair of downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P16: (SEQ ID NO: 32)
catgccatgggccaccaccaccaccaccacacattg tcttctccaa actc

The resulting PCR product of the preceding step was purified, digested with restriction endonucleases Nde I and BamH I, ligated with T4 ligase into the digested vector pET28b with the same endonucleases, cultured on plate and propogated before plasmid isolation, digestion test and preliminary screen of positive clones. The positive clones were then confirmed by DNA sequencing, and the resulting plasmid is named as pET28b-NCPT-1.M1.

2. Construction of a Gene Encoding NCPT-1.M2

Met-Gly amino acid sequence was fused to the N-terminus of NCPT-1 polypeptide, and His-His-His-His-His-His amino acid sequence (SEQ ID NO: 45) was fused to the C-terminus of NCPT-1 polypeptide (MG+NCPT-1+His6).

NCPT-1.M2 polypeptide sequence (SEQ ID NO: 6)
MGTLSSPNSKNEKALGRKINSWESSRSGHSFLSNLHLRNGELVIHE

KGFYYIYSQTYFRFQEEIKENTKNDKQMVQYIYKYTSYPDPILLM

KSARNSCWSKDAEYGLYSIYQGGIFELKENDRIFVSVTNEHLIDM

DHEASFFGAFLVGGGGGRVAAHITGTRGRSNTHHHHHH

PCR was carried out with pET42a-NCPT-1 as a template and P18, P17 as a pair of primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P17: (SEQ ID NO: 33)
cgggatccttagtggtggtggtggtggtgtgtgttgcttcttcctctggt cccagttatgtg P18: (SEQ ID NO: 34)
catgccatgggcacattg tcttctccaa actc The resulting PCR product of the preceding step was purified, digested with restriction endonucleases Nde I and BamH I, ligated with T4 ligase into the digested vector pET28b with the same endonucleases, cultured on plate and propogated before plasmid isolation, digestion test and preliminary screen of positive clones. The positive clones were then confirmed by DNA sequencing, and the resulting plasmid is named as pET28b-NCPT-1.M2.

3. Construction of a Gene Encoding NCPT-1.M3

Met-Gly-His-His-His amino acid sequence (SEQ ID NO: 46) was fused to the N-terminus of NCPT-1 polypeptide (MG+His3+NCPT-1).

NCPT-1.M3 polypeptide sequence (SEQ ID NO: 7)
MGHHHTLSSPNSKNEKALGRKINSWESSRSGHSFLSNLHLRNGEL

VIHEKGFYYIYSQTYFRFQEEIKENTKNDKQMVQYIYKYTSYPDPI

LLMKSARNSCWSKDAEYGLYSIYQGGIFELKENDRI

FVSVTNEHLIDMDHEASFFGAFLVGGGGGRVAAHITGTRGRSNT

PCR was carried out with pET42a-NCPT-1 as a template and P19, P9 as a pair of downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P19: (SEQ ID NO: 35)
catg*ccatgg*gccaccaccacacattg tcttctccaa actc

The resulting PCR product of the preceding step was purified, digested with restriction endonucleases Nde I and BamH I, ligated with T4 ligase into the digested vector pET28b with the same endonucleases, cultured on plate and propogated before plasmid isolation, digestion test and preliminary screen of positive clones. The positive clones were then confirmed by DNA sequencing, and the resulting plasmid is named as pET28b-NCPT-1.M3.

4. Construction of a Gene Encoding NCPT-1.M4

His-His-His-His-His-His gene sequence was fused to the upstream of a gene encoding NCPT-1, i.e. His-His-His-His-His-His amino acid sequence (SEQ ID NO: 45) was fused to the N-terminus of NCPT-1 polypeptide (His6+NCPT-1).

NCPT-1.M4 polypeptide sequence (SEQ ID NO: 8)
HHHHHHTLSSPNSKNEKALGRKINSWESSRSGHSFLSNLHLRNGE

LVIHEKGFYYIYSQTYFRFQEEIKENTKNDKQMVQYIYKYTSYPD

PILLMKSARNSCWSKDAEYGLYSIYQGGIFELKENDRIFVSVTNEH

LIDMDHEASFFGAFLVGGGGGRVAAHITGTRGRSNT

PCR was carried out with pET42a-NCPT-1 as a template and P20, P9 as a pair of downstream and upstream primers using added pfu DNA polymerase (Invitrogen) according to the following parameters on a PCR instrument: 30 cycles of 94° C. denaturation for 1 min, 55° C. annealing for 1 min and 68° C. extension for 1 min, and a final cycle of 68° C. extension for 10 min.

P20: (SEQ ID NO: 36)
catg*catatg*caccaccaccaccacacattg tcttctccaa actc

The resulting PCR product of the preceding step was purified, digested with restriction endonucleases Nde I and BamH I, ligated with T4 ligase into the digested vector pET42a with the same endonucleases, cultured on plate and propogated before plasmid isolation, digestion test and preliminary screen of positive clones. The positive clones were then confirmed by DNA sequencing, and the resulting plasmid is named as pET42a-NCPT-1.M4.

The construction of other mutants, namely NCPT-1.M5, NCPT-1.M6, NCPT-1.M7, NCPT-1.M8, NCPT-1.M9, NCPT-1.M10, NCPT-2.M11, NCPT-3.M12 can be carried out following the above method and "Molecular cloning: a laboratory manual".

Construction of NCPT-1.M5: Met-Gly-His-His-His-His-His-His amino acid sequence (SEQ ID NO: 44) was fused to the N-terminus of NCPT-1 polypeptide using a linker with amino acid sequence of Gly-Ser-Gly-Gly-Gly (SEQ ID NO: 42) (MG+His6+NCPT-1__1linker:GSGGG).

Construction of NCPT-1.M6: Met-Gly-His-His-His-His-His-His amino acid sequence (SEQ ID NO: 44) was fused to the N-terminus of NCPT-1 polypeptide using a linker with amino acid sequence of Gly-Gly-Ser-Gly-Gly-Gly-Gly (SEQ ID NO: 43) (MG+His6+NCPT-1__1linker:GGSGGGG).

Construction of NCPT-1.M7: Met-Gly-His-His-His-His-His-His-His-His-His gene sequence was fused to the upstream of a gene encoding NCPT-1, i.e. Met-Gly-His-His-His-His-His-His-His-His-His amino acid sequence (SEQ ID NO: 47) was fused to the N-terminus of NCPT-1 polypeptide (MG+His9+NCPT-1).

Construction of NCPT-1.M8: Met-Gly and amino acids 129-134 of TRAIL were fused to the N-terminus of NCPT-1 polypeptide (MG+129-134+NCPT-1).

Construction of NCPT-1.M9: Met-Gly-Asn-Asn-Asn-Asn-Asn-Asn gene sequence was fused to the upstream of a gene encoding NCPT-1, i.e. Met-Gly-Asn-Asn-Asn-Asn-Asn-Asn amino acid sequence (SEQ ID NO: 48) was fused to the N-terminus of NCPT-1 polypeptide (MG+Asn6+NCPT-1).

Construction of NCPT-1.M10: Met-Gly amino acid sequence was fused to the N-terminus of NCPT-1 polypeptide, and amino acids 136-141 of TRAIL was fused to the C-terminus of NCPT-1 polypeptide (MG+NCPT-1+aa136-141).

Construction of NCPT-1.M11: Met-Gly-His-His-His-His-His-His gene sequence was fused to the upstream of a gene encoding NCPT-2, i.e. Met-Gly-His-His-His-His-His-His amino acid sequence (SEQ ID NO: 44) was fused to the N-terminus of NCPT-2 polypeptide (MG+His6+NCPT-2).

Construction of NCPT-1.M12: Met-Gly-His-His-His-His-His-His gene sequence was fused to the upstream of a gene encoding NCPT-3, i.e. Met-Gly-His-His-His-His-His-His amino acid sequence (SEQ ID NO: 44) was fused to the N-terminus of NCPT-3 polypeptide (MG+His6+NCPT-3).

NCPT-1.M5 polypeptide sequence (SEQ ID NO: 9)
MGHHHHHHTLSPNSKNEKALGRKINSWESSRSGHSFLSNLHLRN

GELVIHEKGFYYIYS

QTYFRFQEEIKENTKNDKQMVQYIYKYTSYPDPILLMKSARNSCW

SKDAEYGLYSIYQGG IFELKENDRI FVSVTNEHLI

DMDHEASFFGAFLVGGSGGG RVAAHITGTR GRSNT

NCPT-1.M6 polypeptide sequence (SEQ ID NO: 10)
MGHHHHHHTLSSPNSKNEKALGRKINSWESSRSGHSFLSNLHLRN

GELVIHEKGFYYIYS

QTYFRFQEEIKENTKNDKQMVQYIYKYTSYPDPILLMKSARNSCW

SKDAEYGLYSIYQGG

IFELKENDRIFVSVTNEHLIDMDHEASFFGAFLVGGGSGGGRVAA

HITGTRGRSNT

NCPT-1.M7 polypeptide sequence (SEQ ID NO: 11)
MGHHHHHHHHHTLSSPNSKNEKALGRKINSWESSRSGHSFLSNLH

LRNGELVIHEKGFYYIYSQTYFRFQEEIKENTKNDKQMVQYIYKY

TSYPDPILLMKSARNSCWSKDAEYGLYSIYQGGIFELKENDRIFV

SVTNEHLIDMDHEASFFGAFLVGGGGGRVAAHITGTRGRSNT

-continued

NCPT-1.M8 polypeptide sequence (SEQ ID NO: 12)
MGTRGRSNTLSPNSKNEKALGRKINSWESSRSGHSFLSNLHLRNG

ELVIHEKGFYYIYSQTYFRFQEEIKENTKNDKQMVQYIYKYTSYP

DPILLMKSARNSCWSKDAEYGLYSIYQGGIFELKENDRIFVSVTN

EHLIDMDHEASFFGAFLVGGGGGGRVAAHITGTRGRSNT

NCPT-1.M9 polypeptide sequence (SEQ ID NO: 13)
MGNNNNNNTLSPNSKNEKALGRKINSWESSRSGHSFLSNLHLRN

GELVIHEKGFYYIYS

QTYFRFQEEIKENTKNDKQMVQYIYKYTSYPDPILLMKSARNSCW

SKDAEYGLYSIYQGG

IFELKENDRIFVSVTNEHLIDMDHEASFFGAFLVGGGGGRVAAHI

TGTRGRSNT

NCPT-1.M10 polypeptide sequence (SEQ ID NO: 14)
MGTLSPNSKNEKALGRKINSWESSRSGHSFLSNLHLRNGELVIHE

KGFYYIYSQTYFRFQEEIKENTKNDKQMVQYIYKYTSYPDPILLM

KSARNSCWSKDAEYGLYSIYQGGIFELKENDRIFVSVTNEHLIDM

DHEASFFGAFLVGGGGGRVAAHITGTRGRSNTLSSPNS

NCPT-2.M11 polypeptide sequence (SEQ ID NO: 15)
MGHHHHHHTLSPNSKNEKALGRKINSWESSRSGHSFLSNLHLRN

GELVIHEKGFYYIYS

QTYFRFQEEIKENTKNDKQMVQYIYKYTSYPDPILLMKSARNSCW

SKDAEYGLYSIYQGG IFELKENDRI FVSVTNEHLI

DMDHEASFFGAFLVGGGGGG

TSEETISTVQEKQQNISPLVRERGPQRVAAHITGTR GRSNT

NCPT-3.M12 polypeptide sequence (SEQ ID NO: 16)
MGHHHHHHTLSPNSKNEKALGRKINSWESSRSGHSFLSNLHLRN

GELVIHEKGFYYIYS

QTYFRFQEEIKENTKNDKQMVQYIYKYTSYPDPILLMKSARNSCW

SKDAEYGLYSIYQGG IFELKENDRI FVSVTNEHLI

DMDHEASFFGAFLVGGGGGG VRERGPQRVAAHITGTR GRSNT

EXAMPLE 5

Expression and Purification of the Recombinant Human Circularly Permuted Form of TRAIL and Mutant Thereof The expression plasmid was transformed into *E. coli* strain BL21 (DE3), and the transformed *E. coli* was inoculated into 10 ml LB liquid medium containing 20 µg/ml of kanamycin, and cultured on shaking table at 37° C. for 12 hours. 10 ml culture was then inoculated into 1 L LB liquid medium containing 20 µg/ml kanamycin and cultured, when the $OD_{600}$ value reached 0.6, 0.2 ml 1M IPTG was added into 1 L culture to induce protein expression. After 3 hours of induction, the cells were collected by centrifugation, the pellet was suspended in 100 ml buffer containing 100 mM Tris (pH7.9), 150 mM NaCl.

After lysis of the cells by sonication at 4° C., the lysate was centrifuged at 15,000 rpm in a centrifuge with Beckman JA20 rotor. Since the expressed protein can bind to a metal chelate resin, it can be purified by metal chelate chromatography. After centrifugation, the supernatant was pumped into the Ni chromatography column containing the resin, and the contaminating proteins therein were removed by rinse with a buffer containing 50 mM Tris (pH7.9), 0.5M NaCl and 50 mM imidazole. Then the bound protein was eluted with a buffer containing 50 mM Tris (pH7.9), 0.5M NaCl and 200 mM imidazole, and the eluted protein was dialyzed against PBS buffer.

Finally, the protein was purified by the ion exchange column and Superdex 200 (Pharmacia) gel chromatography mounted in AKTA HPLC system (Pharmacia). The purified protein of interest was stored at −80° C., determined for molecular weight and amino acid sequenced etc for further use.

EXAMPLE 6

Assay of Killing Activity of Various Mutants of NCPT-1, NCPT-2, and NCPT-3 on Lung Cancer Cell Line The NCI-H460 cells (ATCC) were cultured in flasks until logarithmic growth phase, digested with 0.25% trypsin (Amresco), collected by centrifugation (1000 rpm, 5 min), resuspended in RPMI1640 medium (Invitrogen) containing 3% fetal bovine serum (FBS), counted and adjusted to $1.5 \times 10^5$/ml cell suspension, added into 96-well culture plates (Nunc) at 100 µl/well, and incubated at 37° C. in 5% $CO_2$ incubator overnight. The sample to be tested was diluted to a certain concentration with 1640 medium containing 3% FBS, and further diluted at 4-fold dilutions (8 dilutions). The supernatant in the culture plate was discarded, and serial dilutions of the sample to be tested was added into the plate at 100 µl/well with a negative control and blank control set aside, incubated at 37° C. under 5% $CO_2$ for 20-24 hours. Following examination under microscope, the supernatant was discarded, each well was added 50 µl 0.05% crystal violet solution (50 mg crystal violet was dissolved in 20 ml anhydrous ethanol, and water was added to the volume of 100 ml, then stored at room temperature) and stained for 3-5 minutes. The crystal violet was carefully washed with flowing water, the remaining water was removed by spin-drying, a destaining solution (50 ml distilled water, 50 ml anhydrous ethanol, and 0.1 ml glacial acetic acid were thoroughly mixed and stored at room temperature) was added at 100 µl/well, then the reading at OD570 was measured on a microplate reader (Bio-Rad 680) (reference wavelength of 630 nm). The inhibitory concentration 50 (IC50) of each sample was calculated by a four-parameter Logistic fitting using Sigmaplot10.0 software. The IC50 for CPT and each mutant of NCPT-1, NCPT-2, and NCPT-3 were calculated, and the activity change of each mutant was represented as a ratio of the IC50 of each mutant to that of CPT (Table 1). The results show that, among various mutants, the activities of NCPT-1.M1, NCPT-1.M2, NCPT-1.M3, NCPT-1.M4, NCPT-1.M5, NCPT-1.M6, NCPT-1.M7, NCPT-2.M11, and NCPT-3.M12 are significantly higher than that of CPT; the activities of NCPT-1.M8 and NCPT-1.M9 are significantly decreased compared to that of CPT; and the activity of NCPT-1.M10 is slightly decreased compared to that of CPT.

| NCPT-1 mutants | Ratio of IC50 of mutants to IC50 of CPT (H460 cells) |
|---|---|
| NCPT-1.M1 | 0.1 |
| NCPT-1.M2 | 0.1 |
| NCPT-1.M3 | 0.4 |
| NCPT-1.M4 | 0.12 |
| NCPT-1.M5 | 0.15 |

-continued

| NCPT-1 mutants | Ratio of IC50 of mutants to IC50 of CPT (H460 cells) |
|---|---|
| NCPT-1.M6 | 0.15 |
| NCPT-1.M7 | 0.3 |
| NCPT-1.M8 | 1.5 |
| NCPT-1.M9 | 3.0 |
| NCPT-1.M10 | 1.2 |
| NCPT-2.M11 | 0.47 |
| NCPT-3.M12 | 0.38 |

EXAMPLE 7

Time-Effect Relationship of NCPT-1. M1 in Killing Tumor Cells In Vitro

Time-Effect Relationship of NCPT-1. M1 in Killing Lung Cancer Cell Line

At 37° C., H460 cells (ATCC) were adherently cultured to logarithmic growth phase in RPMI1640 medium containing 10% FBS in cell culture flask in 5% $CO_2$ incubator. NCPT-1.M1 was added to a final concentration of 50 ng/ml, and cultured for 1 h, 2 h, 4 h and 6 h respectively, and then the cellular morphological changes were observed under inverted phase contrast microscope: in the vehicle control group, at 6 h after the addition of vehicle solution, no morphological changes of cell damage were seen (FIG. 1A); at 1 h after NCPT-1.M1 addition, no obvious morphological changes of H460 cells were seen (FIG. 1B); at 2 h after NCPT-1.M1 addition, morphological changes occurred on some cells: cell shrinkage, cell membrane blebbling, refraction decreased, but detached cells are still rare (FIG. 1C); at 4 h after NCPT-1.M1 addition, the above morphological changes occur on a large number of cells, but the detached cells remain rare (FIG. 1D); at 6 h after NCPT-1.M1 addition, almost all cells exhibited the above morphological changes, detached from the flask bottom, floated and aggregated into pellets, with only a few normal cells scattered (FIG. 1F). At a higher magnification, the cells with morphological changes exhibited the characteristics typical of apoptosis: cytoplasma shrinkage, cell shrinkage, membrane blebbing, resulting in a plurality of apoptotic bodies (FIG. 1E). The results show that, the incubation of NCPT-1.M1 with H460 cells for 1-2 h result in the appearance of morphological apoptosis changes and the incubation for 6 h results in apoptosis of maximum number of cells.

Time-Effect Relationship of NCPT-1.M1 in Killing Multiple Myeloma Cell Line RPMI8226

The time-effect relationship of NCPT-1.M1 in killing human multiple myeloma cell line RPMI8226 (ATCC) was measured using Chemiluminescence (ATPlite Luminescence Assay System, PerkinElmer) method. The cells at logarithmic growth phase were collected by centrifugation (1000 rpm, 5 min), resuspended in 3% FBS-1640 medium, counted and adjusted to $2 \times 10^5$/ml cell suspension, and added into 96-well culture plates at 50 μl/well. The NCPT-1.M1 sample was diluted to 500 ng/ml, 63 ng/ml, 7.8 ng/ml with 3% FBS-1640 medium, the above NCPT-1.M1 samples were added into culture wells containing 50 μl cells at 50 μl/well with the final concentration of NCPT-1.M1 of 250 ng/ml, 31.5 ng/ml, 3.9 ng/ml, the negative control well was added with the same volume of medium without NCPT-1.M1, and all the above were further cultured at 37° C. under 5% CO2. At 1, 3, 6, 8, 24, 48 h after treatment with NCPT-1.M1, the cell lysis buffer were added into plates at 30 μl/well, and shaken for 3 minutes. When the cells were completely lysed, cell lysates were removed and added into chemiluminescence plate at 90 ul/well. Then chemiluminescent substrate solution was added in the plate at 30 μl/well and shaken for 3 minutes, then the readings were measured. Inhibition rate of NCPT-1.M1 on the cells is calculated based on the luminescence intensity of NCPT-1.M1 treated cells and control cells. The results show that, at 1 h of incubation of RPMI 8226 cells with 250 ng/ml, 31.5 ng/ml, 3.9 ng/ml NCPT-1.M1, no inhibitory effect is observed; at 3 h, different degrees of inhibition are detected and follow positive dose-effect relationship; at 6 h, maximum inhibition is reached and is not significantly different from the inhibitory intensity at 8, 24, 48 h (FIG. 2).

EXAMPLE 8

Assay of the Apoptosis-Inducing Activity of NCPT-1.M1 In Vitro

The apoptosis-inducing activity of NCPT-1.M1 on various human tumor cell lines is detected in the present example.

1. Morphological Observation on NCPT-1.M1-Induced Apoptosis of Human Multiple Myeloma Cell RPMI 8226

The RPMI 8226 cells (ATCC) were cultured in cell culture flasks until logarithmic growth phase, collected by centrifugation, resuspended with complete medium (10% FBS-RPMI1640) at $1 \times 10^6$/well, added into 6-well cell culture plate (Costar). The NCPT-1.M1 was diluted with complete medium, added to a final concentration of 200 ng/ml, incubated at 37° C. in 5% CO2 incubator for 3 h. The cells were collected, prepared as smears, fixed with methanol before May-Grünwald-Giemsa (MGG, May-Grünwald stain, commercial available from Beijing ZhongYe HengYuan Chemicals, Giemsa stain, commercial available from Solarbio) staining. At 3 h of incubation of NCPT-1.M1 with cells, the following obvious features of apoptosis were observed: cytoplasma condensation, cell shrinkage, densely staining of chromatin, chromatin aggregation at the periphery of the nucleus, karyopyknosis, karyorrhexis, formation of apoptotic bodies (FIG. 3).

2. TUNEL Staining Showing the Induction of Apoptosis of Human Lung Cancer Cell Line NCI-H460

During the process of apoptosis, the genomic DNA can be broken into double-strand, low molecular weight DNA fragments and high molecular weight single-stranded DNA fragments with broken ends (gaps), and these DNA strand gaps can be identified using enzyme-labeled nucleotide 3'-terminal labeling method. In the case of catalytic action of terminal deoxynucleotidyl transferase (TdT), FITC-labeled nucleotide can be incoporated to the free 3' end nucleotide with template-independent manner, and thereby making the gap of the DNA strand labeled (TUNEL method). The labeling FITC can be recognized by horseradish peroxidase (POD) conjuncated sheep-derived Fab fragment. Upon development with DAB (3,3-diaminobenzidine), the cells stained as brown, which were apoptotic cells, were examined under light microscopy. TUNEL technique is a common method to detect apoptosis. The apoptosis upon incubation of NCI-H460 cell with NCPT-1.M1 was examined using TUNEL technique. NCI-H460 cells (10% FBS-RPMI1640) at logarithmic growth phase were incubated with NCPT-1.M1 (15 ng/ml) for 4 h, then all adherent and floating cells were collected, washed twice with PBS, prepared with PBS into cell suspension, applied on a glass slide, air dried naturally, and fixed in 4% paraformaldehyde for 30 minutes at room temperature. Other procedures were carried out following instructions of TUNEL Apoptosis Detection Kit (ZK-8005, Beijing Zhongshan Golden Bridge Biotechnology Co., Ltd.). The results show that, upon incubation with NCPT-1.M1 (15 ng/ml) for 4 h, a large number of NCI-H460 cells experience apoptosis, exhibiting karyopyknosis, fragmentation into many nuclear fragments, dense brown granules with varying sizes (FIG. 4B). No apoptotic cells are seen in the negative control group (FIG. 4A).

3. Analysis of Internucleosomal DNA Fragmentation in the Apoptotic Cells

NCI-H460 cells at logarithmic growth phase were incubated with NCPT-1.M1 (a final concentration of 15 mg/ml) for 2 h, 4 h, 6 h, and the medium control group was not added with NCPT-1.M1. All adherent and floating cells (approximately $5 \times 10^6$) were collected, and DNA was extracted (Wen Jinkun, Principles and experimental techniques of medical molecular biology, 236-237 (1999)). DNA sample was removed and mixed with 6× loading buffer, and subjected to 1.8% agarose gel (a final concentration of ethidium bromide of 0.5 µg/ml) electrophoresis. The gel was observed under ultraviolet light source and photographed, and analyzed for DNA fragmentation. H460 cells were incubated with NCPT-1.M1 (15 ng/ml) for 2 hours, and its DNA electrophoresis showed obvious ladder, which is the major biochemical feature of apoptosis [Cohen, Advances in Immunol., 50:55-85 (1991)]. To the contrary, in the DNA electrophoresis of the medium control group, a band corresponding to a macromolecule is very near to the loading well, and there is no DNA fragmentation ladder. With the increasing incubation time with NCPT-1.M1, the DNA ladder becomes weaker and vague, and is illegible (FIG. 5), which might be due to DNA being degraded into smaller fragments.

4. Caspase-8 Inhibitor Inhibits the Apoptosis-Inducing Activity of NCPT-1.M1.

H460 cells were incubated with NCPT-1.M1 of 1.2 ng/ml and 10 ng/ml (the culture method is same as the above) for 24 h, and cell survival rates measured by MTT assay were 60% and 16%, respectively. 30 mmol/L Caspase-8 inhibitor zIETD-fmk (Santa Cruz) was added, and 1 h later, 1.2 ng/ml or 10 ng/ml NCPT-1.M1 was added and co-incubated for 24 h, then, the resulting cell survival rates were 100% and 90%, respectively. The results show that Caspase-8 inhibitor blocks the induction of apoptotic activity of NCPT-1.M1 on H460 cells, suggesting that activation of Caspase-8 is involved in the signal transduction pathways of the apoptosis induced by NCPT-1.M1 on H460 cells (FIG. 6).

EXAMPLE 9

Assay of the Apoptosis-Inducing Activity of NCPT-1.M1 In Vivo

Balb/c nu athymic nude mice (Beijing Huafukang Biotechnology Co., Ltd.) were subcutaneously inoculated with human MM RPMI8226 tumor cells. When the tumor grew to the volume of 700-800 mm3, the mice were divided into a control group (n=3) and a CPT treatment group (n=3), and were intraperitoneally injected with control or NCPT-1.M1 at a dose of 15 mg/kg once a day for 3 consecutive days. On day 4, the tumor volumes were measured (method same as the above), all animals were sacrificed, the tumors were resected and fixed in 10% formaldehyde solution. The tumor tissues were embedded in paraffin, cut into sections, and HE stained following the conventional methods. The apoptotic assay of the paraffin-embedded tissue sections were carried out following instructions of TUNEL Apoptosis Detection Kit (ZK-8005, Beijing Zhongshan Golden Bridge Biotechnology Co., Ltd.). Following three consecutive days of treatment with NCPT-1.M1, the average tumor volume was significantly reduced from 798 mm$^3$ before dosing to 286 mm$^3$. HE staining shows a lot of apoptotic cells with condensed and fractured nucleus of blue-black staining, and pale red cytoplasma (FIG. 7B). To the contrary, the nucleus of normal cells are light blue or blue (FIG. 7A). Upon TUNEL staining, the nuclei of apoptotic cells are stained as brown (FIG. 7D). The results show that NCPT-1.M1 treatment can quickly result in apoptosis of a lot of MM tumor cells.

EXAMPLE 10

The Inhibitory Activity of NCPT-1.M1 on Xenograft Tumors in Nude Mice

The inhibitory activity on human colon cancer xenograft tumors:

4 to 5 weeks old Balb/c nu mice ♂ (Institute of Experimental Animals, Chinese Academy of Medical Sciences) were subcutaneously inoculated with COLO 205 human colon tumor tissue pieces. When the tumor grew to the volume of 120 mm3, the tumor-bearing mice were divided into 4 groups (n=7/group), which were intraperitoneally injected with normal saline (negative control group), NCPT-1.M1 5 mg/kg, NCPT-1.M1 15 mg/kg and wtTRAIL 15 mg/kg once a day for 10 consecutive days. Upon the withdrawal, the mice were observed for further 12 days before the end of the experiment. During the experiment, the tumor length diameter (a) and wide diameter (b) were measured every two days with a vernier caliper, and tumor volume (TV) was calculated according to the following formula: TV=½×a×b$^2$; From the above, the relative tumor volume (RTV) was calculated according to following formula: RTV=$V_t/V_0$. Wherein $V_0$ is the tumor volume measured on the day of the administration, but before administration (i.e., d0), and $V_t$ is the tumor volume measured every time. The relative tumor proliferation rate T/C (%) is used as an evaluation index. Evaluation criteria: T/C (%)>40% means no effect; T/C (%)≤40% and the statistical significance of P<0.05 means being effective.

T/C %=RTV$_T$/RTV$_C$*100%. (RTV$_T$: RTV of the treatment group; RTV$_T$: RTV of the negative control group).

As can be seen from Table A, T/C (%) of both two dosage groups of NCPT-1.M1 and wtTRAIL group are all <40%, P<0.05 when compared with the control group, which shows that both two dosage groups of NCPT-1.M1 and wtTRAIL are effective in this tumor model. The efficacy of wtTRAIL with dosage of 15 mg/kg is significantly weaker than that of NCPT-1.M1 with the same dosage (P<0.05), and is comparable to that of NCPT-1.M1 with dosage of 5 mg/kg.

TABLE A

The growth of human COLO 205 xenograft tumor in mice was significantly inhibited by NCPT-1.M1

| Groups | Number of animals | Tumor volume beginning | TV(mm$^3$) ending | relative tumor volume RTV | tumor proliferation rate T/C(%) |
|---|---|---|---|---|---|
| Negative control | 7 | 124 ± 49.1 | 624 ± 246.0 | 4.65 ± 1.667 | |
| NCPT-1.M1 5 mg/kg | 7 | 117 ± 20.4 | 197 ± 146.2 | 1.39 ± 0.571* | 29.89 |

TABLE A-continued

The growth of human COLO 205 xenograft tumor in mice was significantly inhibited by NCPT-1.M1

| Groups | Number of animals | Tumor volume beginning | TV(mm$^3$) ending | relative tumor volume RTV | tumor proliferation rate T/C(%) |
|---|---|---|---|---|---|
| NCPT-1.M1 15 mg/kg | 7 | 118 ± 21.0 | 15 ± 14.6 | 0.12 ± 0.117** | 2.58 |
| wtTRAIL 15 mg/kg | 7 | 127 ± 38.3 | 212 ± 80.7 | 1.58 ± 0.372*# | 33.98 |

*P < 0.05;
**P < 0.001 vs. the negative control group
P < 0.05: vs. CPTm1 15 mg/kg group The inhibitory activity on xenograft tumor of human multiple myeloma:

Athymic nude mice (Beijing Huafukang Biotechnology Co., Ltd.) were subcutaneously inoculated with 5×10$^6$ RPMI8226 tumor cells/mouse. When the tumor grew to the volume of 500 mm3, the mice were divided into several groups, which were intraperitoneally injected with normal saline (negative control group), NCPT-1.M1 (15 mg/kg) and wtTRAIL (15 mg/kg or 45 mg/kg) once a day for 8 consecutive days. The tumor volumes were measured with a caliper every two days. Tumor growth rate of NCPT-1.M1 group with a dose of 15 mg/kg is significantly lower than that of TRAIL group with a dose of 45 mg/kg, suggesting that NCPT-1.M1 has a tumor inhibitory activity stronger on RPMI8226 than that of wild-type TRAIL (FIG. 8).

EXAMPLE 11

The Inhibitory Activity of NCPT-1.M1 Combined with Chemotherapeutics on Human Multiple Myeloma Cell Lines In this example, the tumor-killing effects of NCPT-1.M1 combined with chemotherapeutic agent Melphalan (Glaxo SmithKline) on human multiple myeloma cell line RPMI 8226, H929, U266 B1 (all from ATCC) were measured using chemiluminescence (ATPlite Luminescence Assay System, PerkinElmer) method, wherein both RPMI8226 and H929 are cell lines sensitive to NCPT-1.M1 and U266B1 is insensitive to NCPT-1.M1. The cells at logarithmic growth phase were collected by centrifugation, prepared with RPMI1640 medium containing 10% fetal bovine serum (FBS) into cell suspension at a density of 2×10$^5$~3×10$^5$/ml, and added into 96-well culture plates (NUNC) at 1×10$^4$~1.5×10$^4$/well. The NCPT-1.M1 and melphalan were 2-(or 3- or 4-) serial diluted with the above medium, and melphalan (or NCPT-1.M1) was diluted with NCPT-1.M1 solution (or melphalan sulution) of a certain concentration, added into the above culture plate, incubated at 37° C. in 5% CO$_2$ incubator for 48 h before stopping the reaction, then the chemiluminescence was detected. The cell survival rates were calculated based on the luminous intensity value of the experimental wells and control wells, the results of combination treatment were analyzed using the median efficiency analysis software CalcuSyn V2 (BIOSOFT), and CI means a Combination Index. CI between 0.9 and 1.1 is indicative of an additive effect of the two drugs; CI<0.9 is indicative of a synergistic effect of the two drugs; and CI>1.1 is indicative of an antagonistic effect of the two drugs.

U266B1 is insensitive to NCPT-1.M1, following 48 h incubation with 1 μg/ml NCPT-1.M1, over 80% cells survived. However, the cell survival rate (7.0-62.4%) in the co-presence of melphalan (12.5~50 μg/ml) was significantly lower than that of NCPT-1.M1 alone (85.0%) or melphalan alone (11.9~100.9%), suggesting that the combination of them has an enhanced killing activity (FIG. 9). The combinations of melphalan (12.5 μg/ml) with varying concentrations of NCPT-1.M1 (63~1000 ng/ml) were added to H929 cells sensitive to NCPT-1.M1, and the survival rate was significantly lower than that of the melphalan alone and NCPT-1.M1 alone. There was a synergistic effect of them (CI index of 0.563~0.835) (FIG. 10). Similarly, the combination of melphalan (25 μg/ml) with varying concentrations of NCPT-1.M1 (2~500 ng/ml) were added to RPMI 8226 cells sensitive to NCPT-1.M1, and a synergistic effect of them was observed (CI index of 0.039~0.368) (FIG. 11).

EXAMPLE 12

The Inhibitory Activity of NCPT-1.M1 Combined with Chemotherapeutics on Xenograft Tumors in Nude Mice The inhibitory activity of NCPT-1.M1 combined with melphalan and prednisone on human multiple myeloma xenograft tumor.

Male Balb/c nu athymic nude mice (Beijing Huafukang Biotechnology Co., Ltd.) were subcutaneously inoculated with 5×10$^6$ RPMI8226 tumor cells/mouse. When the tumor grew to about 500 mm$^3$-600 mm$^3$, the mice were divided into normal saline control group (ip.), NCPT-1.M1 group (15 mg/kg, ip, once a day for 10 consecutive days), melphalan (0.75 mg/kg, po., once a day for 5 consecutive days) combined with prednisone group (10 mg/kg, PO. once a day for 10 consecutive days, ig.), NCPT-1.M1 combined with melphalan and prednisone group (dosage, administration method and frequency of each drug were same as the above). The tumor volumes were measured with a caliper every two days. At the end of the experiment, the tumor volumes of NCPT-1.M1 combined with melphalan and prednisone group were significantly lower than that of NCPT-1.M1 monotherapy group and melphalan combined with prednisone group (P<0.05). When these three drugs are combined, the tumors completely disappeared in 57% mice, and in NCPT-1.M1 monotherapy group, the tumors completely disappeared in only 16% mice, and no tumor completely disappeared in melphalan combined with prednisone group. The results suggest that the tumor inhibitory effect of the triple combination of NCPT-1.M1, melphalan and prednisone on RPMI8226 tumor is significantly enhanced (FIG. 12).

The inhibitory effect of NCPT-1.M1 combined with paclitaxel and carboplatin on human lung cancer xenograft tumor.

5-6 weeks old Balb/c nu athymic nude mice ♂ (provided by Institute of Experimental Animals, Chinese Academy of Medical Sciences) were subcutaneously inoculated with NCI-H460 human lung tumor. When the tumor grew to the size of about 150 mm3, the mice were divided into following and administered: normal saline control group (ip.), NCPT-1.M1 monotherapy group (15 mg/kg, i.p., once a day for 9 consecutive days), chemotherapy group (PC regimen: paclitaxel 30 mg/kg i.p. and carboplatin 60 mg/kg i.p., administered once on the first day), NCPT-1.M1 combination chemotherapy group (administration manner and dosage of each drug are same as the above). During the experiment, the tumor length diameter (a) and wide diameter (b) were measured every two days with a vernier caliper, and tumor volume (, TV) is calculated according to the following formula: $TV=\frac{1}{2} \times a \times b^2$. From the above, the relative tumor volume (RTV) was calculated according to following formula: $RTV=V_t/V_0$. Wherein $V_0$ is the tumor volume measured on the day of the administration, but before administration (i.e., d0), and $V_t$ is the tumor volume measured every time. The relative tumor proliferation rate T/C (%) is used as an evaluation index.

$T/C\% = RTV_T/RTV_C * 100\%$. ($RTV_T$: RTV of the treatment group; $RTV_T$: RTV of the negative control group).

As can be seen from Table B, T/C (%) of NCPT-1.M1 monotherapy group and chemotherapy group are 43.9% and 39.8% respectively, and the tumor inhibitory effect of them are significantly improved compared with control group (P<0.05). The T/C (%) of NCPT-1.M1 combination chemotherapy group is 0.8%, which is significantly better than that of NCPT-1.M1 monotherapy group and chemotherapy group (P<0.001). With the NCPT-1.M1 combination chemotherapy, the tumor completely disappear in 66.7% of the mice, while no tumor completely disappear in the other groups, suggesting that the combination of NCPT-1.M1 and chemotherapeutics may have stronger therapeutic effect on those patients with clinical lung cancer (FIG. 13).

TABLE B

The tumor-inhibiting effect of NCPT-1.M1 alone and its combination with paclitaxel and carboplatin on H460 tumor in nude mice

| groups | Number of animals beginning/ ending | Body weight(g) begining | Body weight(g) ending | Tumor size(mm³) begining | Tumor size(mm³) ending | RTV | T/C |
|---|---|---|---|---|---|---|---|
| Negative control | 6  6 | 17.7 ± 2.71 | 18.9 ± 2.84 | 142 ± 74.8 | 1854 ± 458.6 | 16.67 ± 9.218 | |
| NCPT-1.M1 15 mg/kg | 6  6 | 19.9 ± 3.08 | 20.9 ± 3.32 | 156 ± 82.6 | 867 ± 255.7 | 7.32 ± 3.736* ###+++ | 43.9% |
| paclitaxel, carboplatin + NCPT-1.M1 15 mg/kg paclitaxel 30 mg/kg carboplatin 60 mg/kg | 6  6 | 19.4 ± 1.16 | 21.5 ± 1.36 | 172 ± 87.9 | 32 ± 45.2 | 0.13 ± 0.194** | 0.8% |
| paclitaxel 30 mg/kg carboplatin 60 mg/kg | 6  6 | 19.7 ± 1.32 | 21.1 ± 1.07 | 144 ± 42.4 | 962 ± 311.6 | 6.64 ± 0.999* | 39.8% |

Note:
*P < 0.05,
**P < 0.005 vs. the negative control group;
: P < 0.001, vs. the chemotherapy drugs paclitaxel 30 mg/kg and carboplatin 60 mg/kg group alone
+++: P < 0.001, vs. NCPT-1.M1 15 mg/kg group alone

The invention claimed is:

1. A fusion protein comprising a circularly permuted form of tumor necrosis factor (TNF) related apoptosis inducing ligand (TRAIL), which
is the fusion protein whose sequence consists of SEQ ID NO: 5.

2. A pharmaceutical composition for treatment of multiple myeloma comprising the fusion protein according to claim 1, optionally further comprising melphalan.

3. A kit for treatment of multiple myeloma comprising the fusion protein according to claim 1, and optionally melphalan.

4. The kit according to claim 3, wherein the fusion protein and melphalan are mixed together or placed separately.

5. A fusion protein comprising a circularly permuted form of tumor necrosis factor (TNF) related apoptosis inducing ligand (TRAIL), whose sequence is selected from the group consisting of SEQ ID NO: 6-7, 9-11, and 15-16.

6. A pharmaceutical composition for treatment of multiple myeloma comprising the fusion protein according to claim 5, optionally further comprising melphalan.

7. A kit for treatment of multiple myeloma comprising the fusion protein according to claim 5, and optionally melphalan.

8. An isolated nucleic acid encoding the fusion protein according to claim 1 or claim 5.

9. A vector comprising the nucleic acid according to claim 8.

10. A host cell comprising the vector according to claim 9.

11. A method for treatment of tumor, comprising administering to a subject in need thereof the fusion protein according to claim 1 or claim 5.

12. The method according to claim 11, wherein the tumor is selected from the group consisting of multiple myeloma, lymphoma, splenic tumor, melanoma, neuroglioma, mediastinal tumor, ureter tumor, gynecological tumor, endocrine system tumor, central nervous system tumor, lung cancer, colon cancer, gastric cancer, esophageal cancer, intestinal cancer, liver cancer, pancreatic cancer, rectal cancer, kidney adenocarcinoma, bladder cancer, prostate cancer, urethral cancer, testicular cancer, ovarian cancer, breast cancer, leukemia, lung cancer, multiple myeloma and colon cancer.

13. The method according to claim 11, further comprising administering to the subject one or more additional drug(s) for treatment of tumor.

14. The method according to claim 13, wherein the additional drug(s) for treatment of tumor is(are) selected from the group consisting of: melphalan, dexamethasone, thalidomide, lenalidomide, Velcade, vincristine, vinorelbine, doxorubicin, liposomal doxorubicin, cyclophosphamide, irinotecan, prednisone, paclitaxel, carboplatin, cisplatin, VP16, and 5-FU.

* * * * *